(12) United States Patent
Choi et al.

(10) Patent No.: US 10,379,053 B2
(45) Date of Patent: Aug. 13, 2019

(54) PAPER-BASED SURFACE-ENHANCED RAMAN SCATTERING SUBSTRATE, AND PREPARATION METHOD THEREFOR

(71) Applicant: University-Industry Cooperation Group of Kyung Hee University, Gyeonggi-do (KR)

(72) Inventors: Sam Jin Choi, Seoul (KR); Wan Sun Kim, Seoul (KR); Jae-Ho Shin, Seoul (KR); Hun Kuk Park, Seoul (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 0 days.

(21) Appl. No.: 15/578,795

(22) PCT Filed: Jun. 2, 2016

(86) PCT No.: PCT/KR2016/005844
§ 371 (c)(1),
(2) Date: Dec. 1, 2017

(87) PCT Pub. No.: WO2016/195389
PCT Pub. Date: Dec. 8, 2016

(65) Prior Publication Data
US 2018/0080878 A1 Mar. 22, 2018

(30) Foreign Application Priority Data
Jun. 2, 2015 (KR) .......................... 10-2015-0078136

(51) Int. Cl.
*G01N 21/65* (2006.01)
*B82Y 15/00* (2011.01)
(Continued)

(52) U.S. Cl.
CPC ............ *G01N 21/658* (2013.01); *B82Y 15/00* (2013.01); *B82Y 20/00* (2013.01); *G01J 3/44* (2013.01);
(Continued)

(58) Field of Classification Search
CPC .. G01N 21/658; G01N 21/8483; B82Y 15/00; B82Y 20/00; B82Y 30/00; G01J 3/44; G01J 33/487; G01J 33/54373
(Continued)

(56) References Cited

U.S. PATENT DOCUMENTS

2006/0163087 A1* 7/2006 Allen .................. B01J 19/0093
205/775
2006/0177705 A1* 8/2006 Ahner .................. B82Y 10/00
428/832
(Continued)

FOREIGN PATENT DOCUMENTS

KR 10-2014-0122066 10/2014

OTHER PUBLICATIONS

Lee et al. Design and fabrication of paper microfluidic channel, vol. 14, No. 4, pp. 525-530, Dec. 2011.
(Continued)

*Primary Examiner* — Hina F Ayub
(74) *Attorney, Agent, or Firm* — Parker Highlander PLLC

(57) ABSTRACT

The present invention relates to: a paper-based surface-enhanced Raman scattering (SERS) substrate comprising metal nanoparticles, which are uniformly distributed and adsorbed on a designed pattern and have a diameter of 1 nm to 100 nm; a point-of-care (POC) diagnostic kit, comprising the paper-based SERS substrate; and a method for preparing the paper-based SERS substrate.

15 Claims, 18 Drawing Sheets

(51) Int. Cl.
  *B82Y 20/00* (2011.01)
  *G01J 3/44* (2006.01)
  *G01N 33/487* (2006.01)
  *G01N 33/543* (2006.01)
  *B82Y 30/00* (2011.01)
  *G01N 21/84* (2006.01)

(52) U.S. Cl.
  CPC ..... *G01N 33/487* (2013.01); *G01N 33/54373* (2013.01); *B82Y 30/00* (2013.01); *G01N 21/8483* (2013.01)

(58) Field of Classification Search
  USPC .......................................................... 356/301
  See application file for complete search history.

(56) References Cited

U.S. PATENT DOCUMENTS

| | | | | |
|---|---|---|---|---|
| 2007/0003716 | A1* | 1/2007 | Suzuki | B41M 5/502 428/32.36 |
| 2010/0323014 | A1* | 12/2010 | Bloom | A61K 9/5138 424/486 |
| 2011/0303885 | A1* | 12/2011 | Vanheusden | H01B 1/22 252/513 |
| 2012/0184451 | A1* | 7/2012 | Singamaneni | B82Y 5/00 506/9 |
| 2013/0084630 | A1* | 4/2013 | Rolland | G01N 21/78 435/287.8 |
| 2013/0209692 | A1* | 8/2013 | Zinn | H01B 1/22 427/376.6 |
| 2014/0176941 | A1* | 6/2014 | Romero Fanego | G01N 21/65 356/301 |
| 2015/0240100 | A1* | 8/2015 | Liu | C09D 11/037 252/514 |
| 2017/0045456 | A1* | 2/2017 | Fabris | G01N 21/658 |
| 2017/0342661 | A1* | 11/2017 | Aulin | D21H 23/50 |

OTHER PUBLICATIONS

Lin, Xiu-Mei et al. 'Surface-enhanced Raman spectroscopy: substrate-related issues', Analytical and Bioanalytical Chemistry 394, Apr. 19, 2009, pp. 1729-1745.

Martinez, Andres W. et al. 'Patterned Paper as a Platform for Inexpensive, Low Volume, Portable Bioassays', Angew Chem Int Ed Engl. 46(8), Jan. 9, 2007, pp. 1318-1320.

Mehn, Dora et al. 'Immobilised gold nanostars in a paper-based test system for surface-enhanced Raman spectroscopy' Vibrational Spectroscopy 68, May 30, 2013, pp. 45-50.

Ngo, Ying Hui et al. 'Effect of cationic polyacrylamides on the aggregation and SERS performance of gold nanoparticles-treated paper', Journal of Colloid and Interface Science 392, Oct. 22, 2012, pp. 237-246.

Ren, Bin et al. 'Raman spectroscopy on transition metals', Analytical and Bioanalytical Chemistry 388, Feb. 21, 2007, pp. 29-45.

Renault, Christophe et al. 'Electrochemistry in Hollow-Channel Paper Analytical Devices', Journal of the Ametican Chemical Society 136(12), Mar. 17, 2014, pp. 4616-4623.

Wei, Xiaoyi et al. 'A colorimetric sensor for determination of cysteine by carboxymethyl cellulose-functionalized gold nanoparticles', Analytica Chimica Acta 671, May 11, 2010, pp. 80-84.

Zeng, Shuwen et al. 'Nanomaterials enhanced surface plasmon resonance for biological and chemical sensing applications', Chemical Society Reviews 43, Feb. 18, 2014, pp. 3426-3452.

* cited by examiner

FIGS. 1A-C
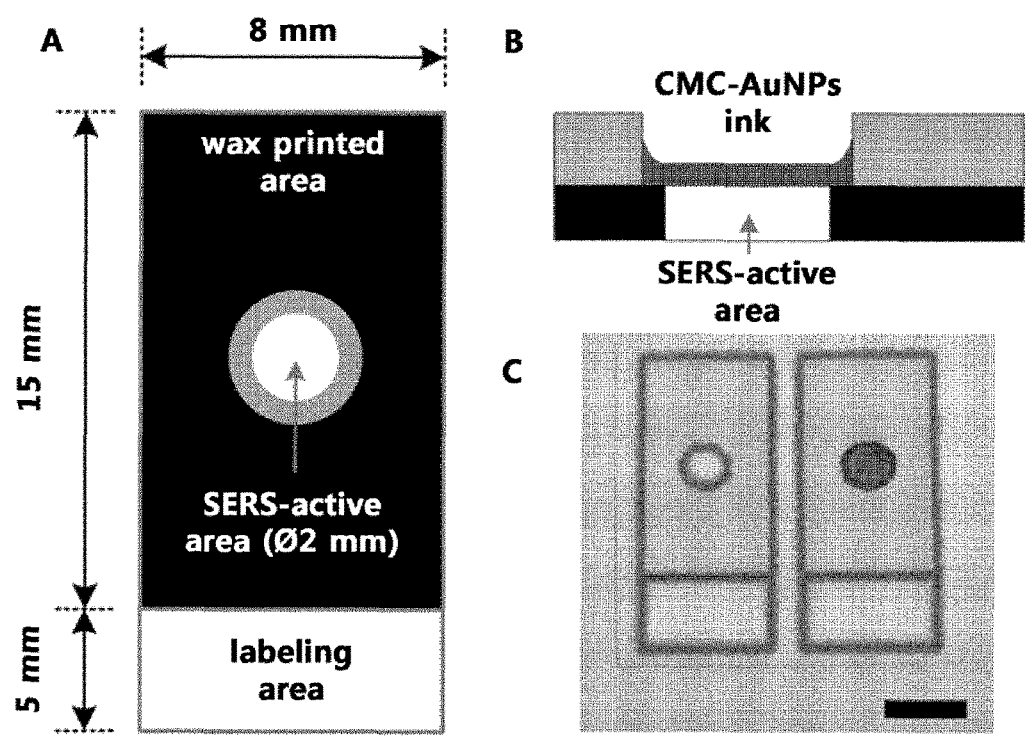

FIGS. 2A-D
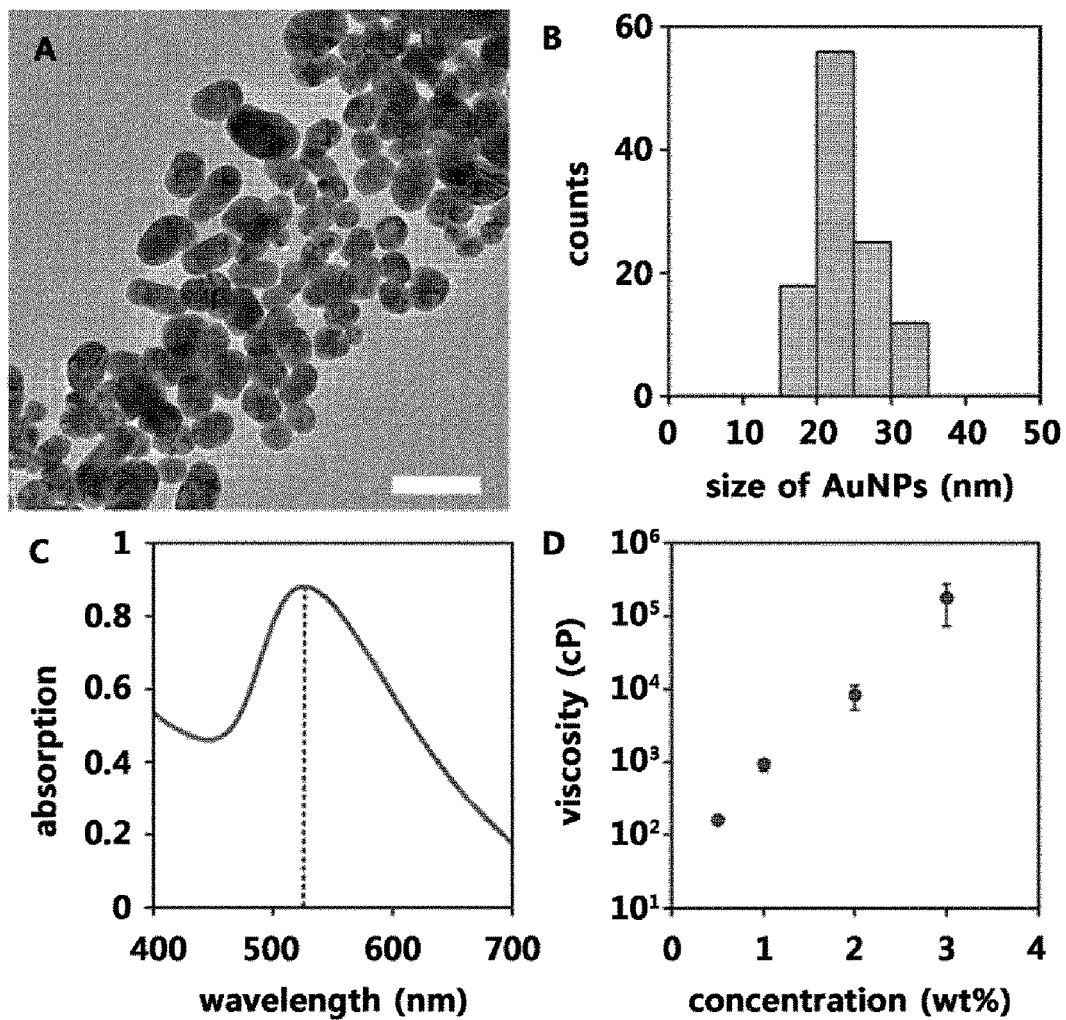

FIGS. 3A-C
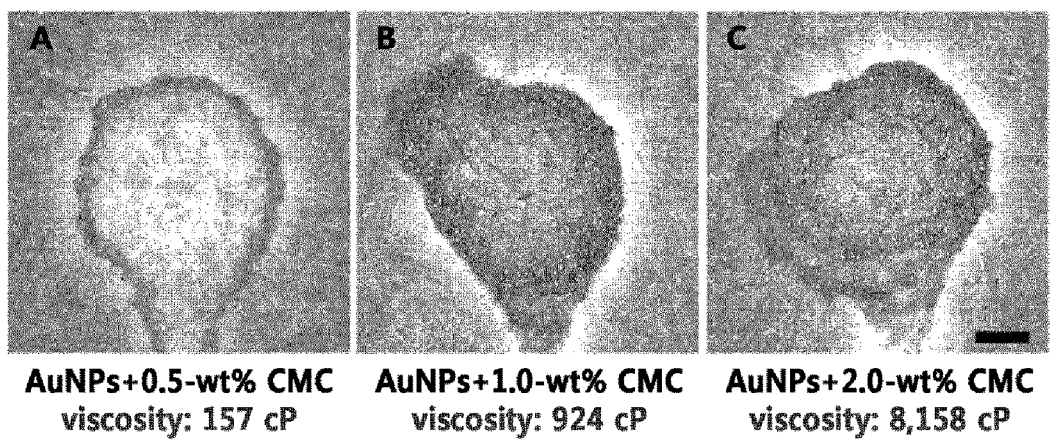
AuNPs+0.5-wt% CMC
viscosity: 157 cP
AuNPs+1.0-wt% CMC
viscosity: 924 cP
AuNPs+2.0-wt% CMC
viscosity: 8,158 cP
FIGS. 4A-B
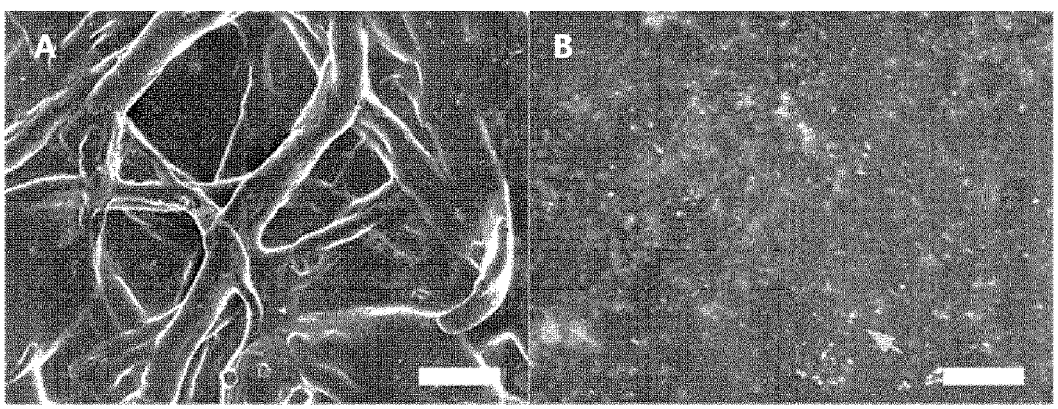

FIGS. 5A-B
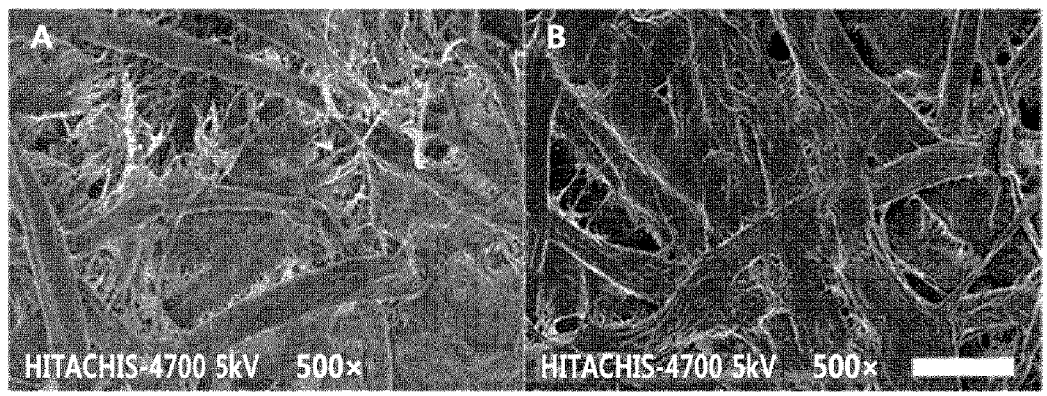

FIG. 12
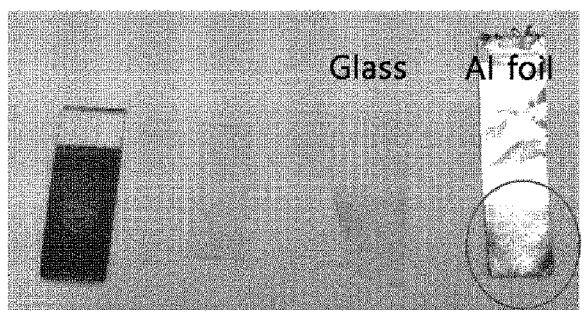
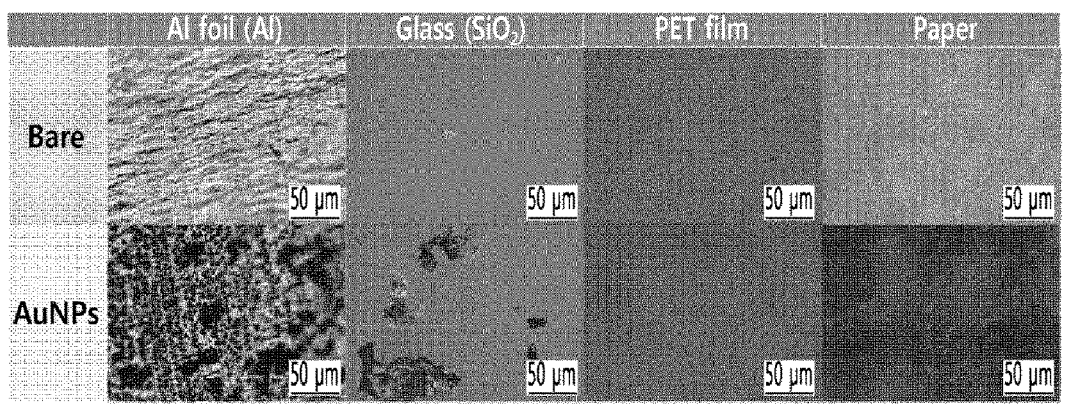

PAPER-BASED SURFACE-ENHANCED RAMAN SCATTERING SUBSTRATE, AND PREPARATION METHOD THEREFOR

This application is a national phase application under 35 U.S.C. § 371 of International Application No. PCT/KR2016/005844, filed Jun. 2, 2016, which claims priority to Korean Application No. 10-2015-0078136, filed Jun. 2, 2015 and to Korean Patent Application No. 10-2015-0096158 filed Jul. 6, 2015. The entire text of each of the above referenced disclosures is specifically incorporated herein by reference.

TECHNICAL FIELD

The present invention relates to a paper-based surface-enhanced Raman scattering (SERS) substrate comprising metal nanoparticles having a diameter of 1 nm to 100 nm uniformly distributed and adsorbed in a designed pattern; a point-of-care (POC) diagnostic kit, comprising the paper-based SERS substrate; and a method for preparing the paper-based SERS substrate.

BACKGROUND ART

Raman spectroscopy is a technique that provides molecular-specific information on biological and chemical samples. However, since Raman signals are intrinsically very weak, various studies have been conducted to enhance the same. Surface-enhanced Raman scattering (SERS) activity can significantly enhance the intensity of the Raman spectra due to absorption energy at a surface. The enhancement factor (EF) used as a measure of the scale of SERS is normally in the range of $10^4$ to $10^8$ and may even reach $10^{14}$, which allows detection of single molecules. Most studies with respect to the increase of SERS EF are focused on surface materials and substrate-related fields through modification with nanostructure patterns. Most SERS-active moieties have been prepared by comprehensive and sophisticated methods including lithography or high-temperature processes. While these methods of producing SERS-active substrates involve long, complex steps with a risk of explosion, the use of metal nanoparticles as a SERS substrate provides an easy method of synthesis at low cost and allows size and shape adjustment by reaction conditions, and also agglomerated nanoparticles can significantly improve signaling, thereby providing sensitivity of detection at the level of single molecules (X. M. Lin et al., *Anal. Bioanal. Chem.*, 2009, 394: 1729 to 1745). These nanoparticles exhibit an optical property that absorbs wavelengths used in Raman laser light sources, that is, surface plasmon resonances (SPR) (S. Zeng et al., *Chem. Soc. Rev*, 2014, 43: 3426 to 3452). In particular, gold, silver, and copper nanoparticles can achieve $10^3$-fold greater enhancement of SERS than other metal substrates (B. Ren et al., *Anal. Bioanal. Chem.*, 2007, 388: 29 to 45). Silver nanoparticles (AgNPs) exhibit superior SERS enhancement compared to gold nanoparticles (AuNPs). However, AgNPs are oxidized in the atmosphere and thus their SERS activity is rapidly reduced, whereas AuNPs form oxide layers and thereby exhibit stable SERS activity.

Meanwhile, paper substrates with economic efficiency (low cost), portability, flexibility, ease of handling, and harmlessness are drawing attention as a novel platform for analytical detection in biomedical and environmental fields (A. W. Martinez et al., *Angew. Chemie—Int. Ed.*, 2007, 46: 1318 to 1320). These user-friendly advantages enable a variety of applications including colorimetric, electrochemical, and biochemical analyses using paper (C. Renault et al., *J. Am. Chem. Soc.*, 2014, 136: 4616 to 4623). These advantages of paper substrates are suitable for point-of-care (POC) applications, but the utilization of paper substrates has a problem in that the restricted detection limit of analytes due to the use of enzymes and redox dyes, and the handling of composite soluble compounds must be overcome.

DISCLOSURE

Technical Problem

The present inventors have made many efforts to develop a method for manufacturing a SERS-active platform, in which metal nanoparticles are introduced on a paper substrate, at low cost and by a simple process. As a result, they have discovered that when metal nanoparticles are uniformly formed on the surface of a substrate using a continuous chemical reaction method in a series of aqueous solutions, or when a solution containing metal nanoparticles has its viscosity adjusted by the addition of a predetermined amount of carboxymethylcellulose and is coated on a paper substrate having a desired pattern formed thereon, it is possible to distribute the SERS-active parts uniformly at regular intervals without the coffee ring phenomenon, whereby the particles are concentrated at the edges of the pattern, and thus the signal enhancement effect can be exhibited in the entirety of the active parts, thus confirming that it is possible to provide a paper-based SERS substrate which is easy to carry and is suitable for point-of-care (POC) diagnosis and provides reproducible results, and thereby the present invention was completed.

Technical Solution

An object of the present invention is to provide a paper-based surface-enhanced Raman scattering (SERS) substrate comprising metal nanoparticles having a diameter of 1 nm to 100 nm uniformly distributed and adsorbed in a designed pattern.

Another object of the present invention is to provide a point-of-care (POC) diagnostic kit comprising the paper-based SERS substrate.

Still another object of the present invention is to provide a method for preparing the paper-based SERS substrate, comprising: step (1) of immersing a paper substrate in a precursor solution of a $1^{st}$ metal for the adsorption of precursors of the $1^{st}$ metal on the substrate; step (2) of immersing the paper substrate, on which the precursors of the $1^{st}$ metal are adsorbed, in a $1^{st}$ buffer for washing; step (3) of immersing the washed paper substrate in a solution of a $1^{st}$ reducing agent to form nanoparticles of the $1^{st}$ metal; and step (4) of immersing the nanoparticles of the $1^{st}$ metal grown on the paper substrate in a $1^{th}$ buffer for washing.

Still another object of the present invention is to provide a method for preparing the paper-based SERS substrate, comprising: step (1) of preparing a solution of metal nanoparticles by mixing metal nanoparticles and an aqueous solution of carboxymethylcellulose; step (2) of preparing a paper substrate on which a desired pattern is formed; and step (3) of coating the solution of metal nanoparticles of step (1), on the paper substrate.

Advantageous Effects of the Invention

The paper-based SERS substrate according to the present invention can be easily prepared at low cost by a simple process by a continuous chemical reaction method or coating with a metal nanoparticle-dispersed solution having a predetermined viscosity which further comprises carboxymethylcellulose, following impregnation of an area other than areas on which the SERS-active pattern is to be formed, with a hydrophobic material, such as a wax.

Furthermore, the preparation method using the continuous chemical reaction method has advantages in that the method can be based on paper with low cost and carried out in an aqueous solution. Since the method is based on paper having high absorption capability, a greater surface area can be provided, and reactants can be easily adsorbed and thus uniformly distributed throughout the designed area, and as a result, when the metal nanoparticles are formed by reducing the adsorbed reactants, and the nanoparticles formed are uniformly distributed throughout the active area, thereby exhibiting reproducible SERS activity.

Meanwhile, by using the substrate, which was prepared by a method of coating the metal nanoparticle-dispersed solution which acquires a predetermined viscosity by further containing carboxymethylcellulose therein, the metal nanoparticles are uniformly distributed over the entire designed area by minimizing the coffee ring phenomenon where the particles are concentrated at the interface of the patterns, thereby exhibiting uniform SERS activity and reproducible results.

In particular, all of the substrates according to the present invention are not only able to exhibit synergistic enhancement of signal in the presence of additional Raman-active material, but it can also be useful as a point-of-care (POC) diagnostic kit with improved sensitivity because it is light, easy to handle, and easy to carry due to its paper-based properties.

BRIEF DESCRIPTION OF DRAWINGS

FIGS. 1A-C are schematic diagrams showing a SERS platform according to the present invention; in which (A) shows a design of the SERS platform in which gray (hydrophobic) shows a reduced size due to wax penetration; (B) shows a cross-sectional view of the SERS-active area formed on a paper substrate; and (C) shows an image of a paper substrate before and after printing with the CMC-AuNPs ink (scale; 5 mm).

FIGS. 2A-D show the results of analysis with respect to characteristics of AuNPs and CMC solutions; in which (A) shows a TEM image of synthesized AuNPs (scale; 50 nm); (B) shows a graph with respect to the size distribution of AuNPs; (C) shows a graph with respect to a UV-Vis absorption spectrum of colloidal AuNPs; and (D) shows a graph with respect to the viscosity of the CMC solution at four different concentrations.

FIGS. 3A-C show images with respect to the distribution of AuNPs on a paper substrate prepared using the CMC solution at three different concentrations (scale; 500 μm).

FIGS. 4A-B show images with respect to the distribution of AuNPs on a paper substrate according to the present invention; in which (A) shows an SEM image of the CMC-AuNPs ink loaded on a paper substrate (scale; 50 μm); (B) shows an image with respect to the distribution of AuNPs (arrows) on a paper substrate (scale; 500 nm).

FIGS. 5A-B show images with respect to the surface morphology of (A) a bare paper and (B) a wax-impregnated paper (scale; 50 μm).

FIG. 12 shows images with respect to the appearance and microscopic surface structures of the SERS substrates prepared by applying a continuous chemical reaction method to various substrates according to Example 1 and Comparative Examples 1 to 3 of the present invention.

BEST MODE

Figure 6:
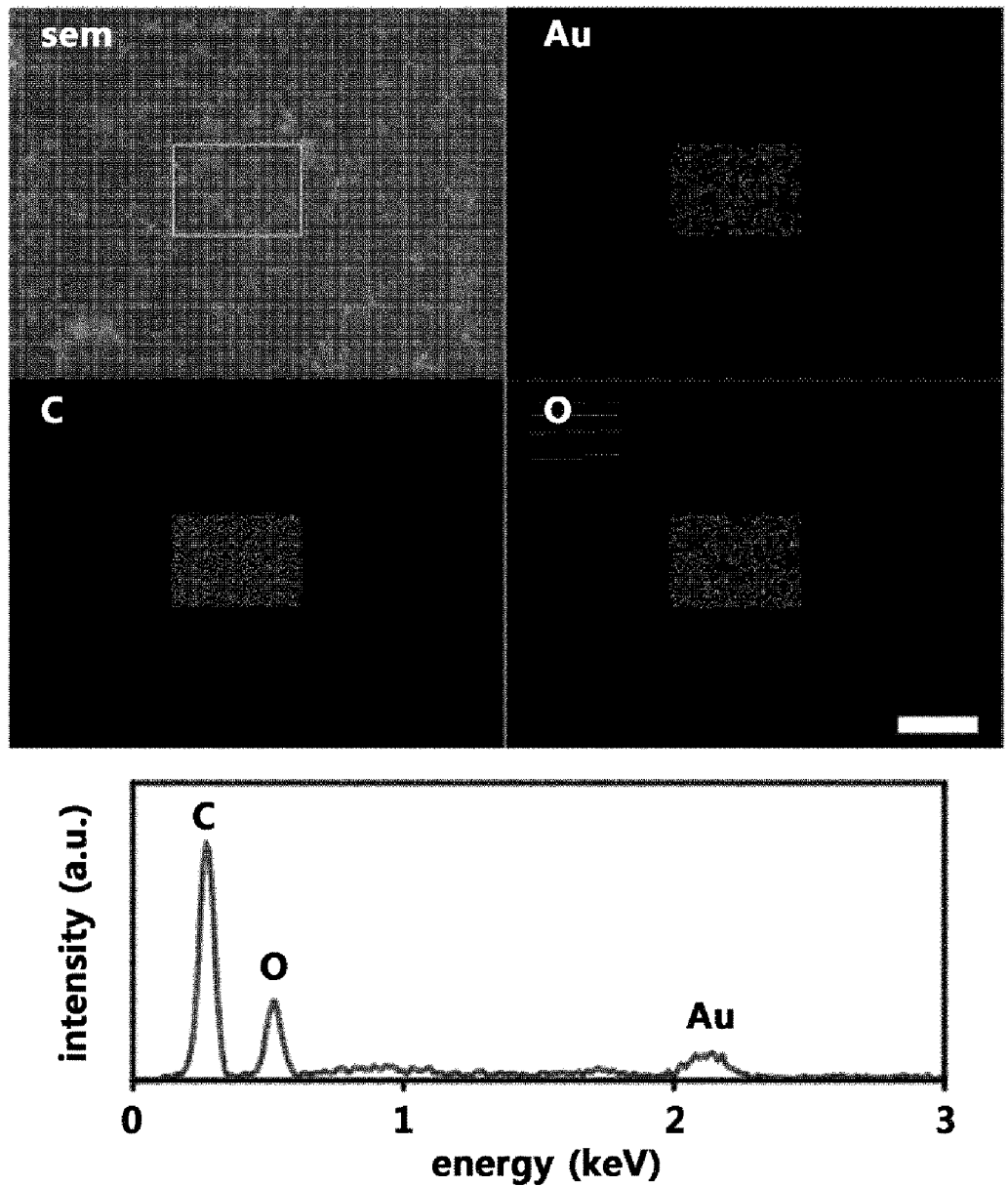
FIG. 6 shows images with respect to EDX spectroscopic analysis and a graph with respect to the mapping finding results of a CMC-AuNPs-printed paper substrate (scale; 500 nm).

To achieve the above objects, a first aspect of the present invention provides a paper-based based surface-enhanced Raman scattering (SERS) substrate, which comprises metal nanoparticles having a diameter of 1 nm to 100 nm uniformly distributed and adsorbed in a designed pattern.

A second aspect of the present invention provides a point-of-care (POC) diagnostic kit comprising the paper-based SERS substrate according to the first aspect of the present invention.

A third aspect of the present invention provides a method for preparing the paper-based SERS substrate according to the first aspect of the present invention, which comprises: step (1) of immersing a paper substrate in a precursor solution of a $1^{st}$ metal for the adsorption of precursors of the $1^{st}$ metal on the substrate; step (2) of immersing the paper substrate, on which the precursors of the $1^{st}$ metal are adsorbed, in a $1^{st}$ buffer for washing; step (3) of immersing the washed paper substrate in a solution of a $1^{st}$ reducing agent to form nanoparticles of the $1^{st}$ metal; and step (4) of immersing the nanoparticles of the $1^{st}$ metal grown on the paper substrate in a $1'^{th}$ buffer for washing.

A fourth aspect of the present invention provides a method for preparing the paper-based SERS substrate according to the first aspect of the present invention, which comprises: step (1) of preparing a solution of metal nanoparticles by mixing metal nanoparticles and an aqueous solution of carboxymethylcellulose; step (2) of preparing a paper substrate on which a desired pattern is formed; and step (3) of coating the solution of metal nanoparticles of step (1), on the paper substrate.

Hereinafter, the present invention is described in detail.

The present invention relates to a paper-based SERS substrate which can be easily obtained even at low cost and a preparation method thereof. For example, paper is made of fibers and thus has a rough fibrous texture on a microscopic scale. In general, considering that SERS exhibits the effect of enhancing the Raman scattering signal on a rough surface, a method of utilizing the texture of the paper can be considered. However, the texture of paper surface is due to irregularly-arranged fibers, and that irregularity may induce the irregular distribution of metal nanoparticles being introduced onto the surface (for example, metal nanoparticles are accumulated in the depressed area at high density while present sparsely in the protruded area) and cause difficulty in detecting reproducible signals or the signals and reduction of the signals due to the offset caused by the phase mismatch of the generated signals. Accordingly, it is necessary to develop a method for uniform distribution of metal nanoparticles so as to avoid the disadvantages that may occur by the irregular surface structure while taking the advantages provided by using a paper substrate.

As part of the effort, the present invention can not only be easily carried out in an aqueous solution by the continuous chemical reaction method (i.e., repeating the steps of immersing in a series of reaction solutions sequentially and washing with a buffer), but it can also provide a greater surface area because it is based on a paper with good absorbency, and thereby provide uniform distribution over the entire designed area due to easier adsorption of reactants. As a result, it was discovered that when reducing those uniformly adsorbed reactants, the nanoparticles formed were uniformly distributed over the entire active area and thus could exhibit reproducible SERS activity. Additionally, it was confirmed that when a method is used wherein an area other than those areas where the SERS-active pattern is to be formed is impregnated with a hydrophobic substance such as a wax, followed by coating a solution, in which metal nanoparticles are dispersed, having a predetermined level of viscosity by further comprising carboxymethylcellulose, the coffee ring phenomenon of particles being concentrated at the interface of the pattern can be minimized while exhibiting the effect of lowering the roughness of the paper surface by filling the irregular paper surface with carboxymethylcellulose, thereby enabling uniform distribution of metal nanoparticles over the entire designed area and also providing reproducible results as well as even SERS activity.

The present invention provides a paper-based SERS substrate comprising metal nanoparticles having a diameter of 1 nm to 100 nm uniformly distributed and adsorbed in a designed pattern.

In the conventional method of adsorption by coating the already-formed metal nanoparticles having a predetermined size to a substrate or preparing in the form of a thin film, in general, nanoparticles of several tens of nanometers is used or a thin metal layer of several tens of nanometers is formed. In contrast, the method of the present invention for growing nanoparticles by adsorbing a metal precursor on a substrate and reducing the same by treating with a reducing agent enables the formation of particles at a level of several nanometers by adjusting the reaction time and the number of repetitions, and thus can provide significantly improved SERS due to a superior surface plasmon resonance effect.

Specifically, the metal nanoparticles may have a diameter of 1 nm to 30 nm, and more specifically, a diameter of 1 nm to 10 nm, but the size of the diameter is not limited thereto.

For example, the paper-based SERS substrate of the present invention may further comprise carboxymethylcellulose. The carboxymethylcellulose can fill the irregular rough surface formed by the fibers present on a paper substrate itself to have a relatively uniform surface and thereby exhibit an effect of uniform SERS over the entire Raman-active area. In particular, the metal nanoparticles included in the paper-based SERS substrate according to the present invention may have a uniform size with an average diameter of 10 nm to 100 nm, and more specifically 10 nm to 50 nm.

A second aspect of the present invention provides a point-of-care (POC) diagnostic kit comprising the paper-based SERS substrate according to the first aspect of the present invention.

The POC diagnostic kit can be used for qualitative and/or quantitative analysis of target analytes in various fields such as medicine, agriculture, animal husbandry, food, military, environment, etc., as well as diagnosis or tests of various kinds of diseases. For example, the POC diagnostic kit can be used to detect target analytes from biological samples such as whole blood, blood cells, serum, plasma, bone marrow fluid, sweat, urine, tears, saliva, skin, mucous membrane, hair, etc. isolated from mammal, specifically, humans. Alternatively, the POC diagnostic kit can be used to detect environmental pollutants, specifically, chemical compounds in waste water and sewage, but the applications thereof are not limited thereto.

The POC diagnostic kit of the present invention is characterized by being able to qualitatively and/or quantitatively detect a target analyte in a given sample by Raman spectroscopy.

Specifically, the POC diagnostic kit comprising a paper-based SERS substrate according to the present invention can exhibit synergistic enhancement of signal when an additional Raman-active material is present. At this time, the Raman spectrum remains unchanged, i.e., a spectrum of increased intensity at the same peak position can be provided. The Raman-active material includes, without limitation, Raman-active materials known in the art. Specifically, the Raman-active material may be Rhodamine B, Rhodamine 6G, and 2-naphthalenethiol (2-NAT), but is not limited thereto.

According to a specific embodiment of the present invention, when a Raman-active molecule (e.g., Rhodamine B) was coated on a paper-based SERS substrate which additionally comprises carboxymethylcellulose according to the present invention, a significantly increased Raman signal was observed even at a concentration of 1/1000, compared to when the Raman-active molecule was coated on a bare paper substrate. In Experimental Example 5 of the present invention, with respect to the intensity of Raman signal at the 1356 cm$^{-1}$ band, the intensity was shown to be 328 when Rhodamine B was treated on a bare paper at a concentration of 1 M, whereas the intensity was shown to be 5858 when Rhodamine B was treated on the paper-based SERS substrate according to the present invention at a concentration of 1 mM, thus confirming that an approximately 18-fold increase of Raman signal was exhibited even when the Raman-active molecule was treated on the paper-based SERS substrate according to the present invention, even though applied at an 1/1000 concentration.

According to another specific embodiment of the present invention, an approximately 1000-fold increase of Raman signal was observed when Rhodamine B was coated as a Raman-active molecule on a SERS substrate prepared according to the continuous chemical reaction method, compared to when Rhodamine B was coated on a bare paper, although Rhodamine B was treated at the same concentration on both substrates. In Experimental Example 8 of the present invention, with respect to the intensity of Raman signal at the 1201 cm$^{-1}$ band, the intensity was shown to be 31 when Rhodamine B was treated on a bare paper at a concentration of 1 mM, whereas the intensity was shown to be 29328, which was an approximately 1,000-fold increase of Raman signal, when Rhodamine B was treated on the paper-based SERS substrate according to the present invention at the same concentration.

Figure 15:
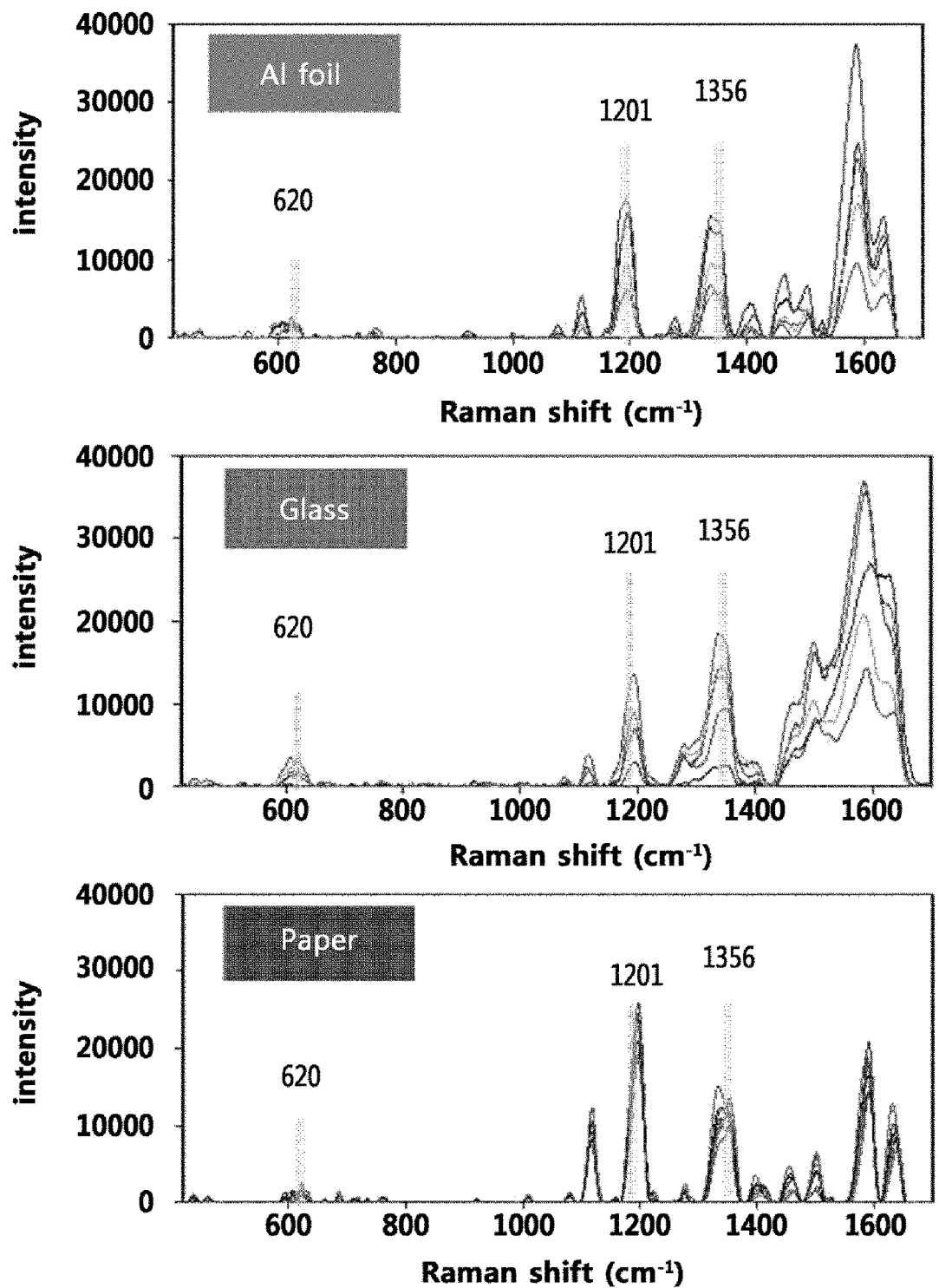
FIG. 15 shows the results with respect to the deviation of the Raman signal of RhB measured 5 times independently on SERS substrates prepared by the continuous chemical reaction method based on aluminum foil, glass, and paper, respectively.

Additionally, the surface shapes of substrates were observed when the continuous chemical reaction method was carried out on substrates other than a paper substrate. For example, when the reaction was carried out using aluminum foil or glass as a substrate, the metal nanoparticles formed were non-uniformly distributed on the substrate, thus exhibiting different values of the Raman signal depending on the number of measurements for the same sample, and remarkably low reproducibility of the measurement. Meanwhile, when the reaction was carried out on a paper substrate, the metal nanoparticles formed were uniformly distributed on the substrate, thus exhibiting an effect of reproducible signal enhancement even under the same reaction conditions (FIGS. 12 and 15).

As such, the POC diagnostic kit comprising a paper-based SERS substrate according to the present invention can exhibit the effect of significant increase of Raman intensity and provide reproducible results, and thus the POC diagnostic kit can be used to analyze trace samples in combination with Raman spectroscopy.

The samples that can be analyzed by the POC diagnostic kit may be biological samples such as tears, blood components, sweat, urine, etc.; various chemical materials; environmental pollutants; etc. When the target analyte contains a Raman-active molecule, it can be directly analyzed without an additional labeling material. Otherwise, the target analyte in the sample can be analyzed by labeling with a Raman-active material.

The paper-based SERS substrate according to the present invention may be prepared by a method which comprises: step (1) of immersing a paper substrate in a precursor solution of a $1^{st}$ metal for the adsorption of precursors of the $1^{st}$ metal on the substrate; step (2) of immersing the paper substrate, on which the precursors of the $1^{st}$ metal are adsorbed, in a $1^{st}$ buffer for washing; step (3) of immersing the washed paper substrate in a solution of a $1^{st}$ reducing agent to form nanoparticles of the $1^{st}$ metal; and step (4) of immersing the nanoparticles of the $1^{st}$ metal grown on the paper substrate in a $1^{'th}$ buffer for washing.

For example, steps (1) to (4) may be repeatedly performed 2 to 10 times so as to form particles with an appropriate size, but the number of repetitions is not limited thereto.

Furthermore, a substrate on which composite nanoparticles comprising the $1^{st}$ and $2^{nd}$ metals are formed may be prepared by further performing: step (1)' of immersing the paper substrate obtained from step (4) in a precursor solution of a $2^{nd}$ metal for the adsorption of $2^{nd}$ metal precursors on the substrate; step (2)∝ of immersing the paper substrate, on which the $2^{nd}$ metal precursors are adsorbed, in a $2^{nd}$ buffer for washing; step (3)' of immersing the washed paper substrate in a solution of a $2^{nd}$ reducing agent to form nanoparticles of the $2^{nd}$ metal; and step (4)' of immersing the nanoparticles of the $2^{nd}$ metal grown on the paper substrate in a $2^{'th}$ buffer for washing.

For example, steps (1)' to (4)' may be repeatedly performed 2 to 5 times so as to form particles with an appropriate size, but the number of repetitions is not limited thereto.

For example, steps (1) and (1)' may be each independently performed for 10 to 120 seconds and steps (3) and (3)' may be each independently performed for 10 to 120 seconds, but the time for performance is not limited thereto.

Considering steps (1)' to (4)' as a single set, when step (1) (or step (1)') and/or step (3) (or step (3)') are performed for less than 10 seconds, the metal precursors may not be sufficiently adsorbed or the reaction by a reducing agent may not be properly completed, and thus the formation of nanoparticles may be incomplete, thereby making it difficult to expect reproducibility. Meanwhile, when each step is performed for about 120 seconds, it is enough to complete the adsorption of the metal precursors or the formation of metal particles by the reducing agent, and if each step is performed in excess of the above time it may cause unnecessary waste of time and side reactions.

The number of repetitions with respect to steps (1)' to (4)' and steps (1)' to (4)' may be appropriately selected at a level that can maximize the SERS effect by those skilled in the art, considering the concentration of the precursor solution and/ or the solution of a reducing agent and the time for performing each step, etc.

The paper used as a substrate in the present invention, which can be easily obtained even at low cost, is a substrate comprised of fibers, and the paper was shown by microscopic observation to have a rough texture of irregularly-arranged fibers. Unlike other substrates comprised of metallic or inorganic materials, the surface of a paper, for example, includes micropores formed by entanglement of fibers together. Due to such a structure, a paper substrate allows fluids to not simply adsorb thereto but instead to impregnate thereinto by capillary force and be stored therein. Accordingly, when a reaction is carried out after letting a paper substrate absorb a reaction solution, a greater surface area can be provided (FIG. 5A).

For example, a pattern may be formed on a paper substrate by treating an area of the paper substrate other than the SERS-active area to be formed with a hydrophobic material prior to reactions. Specifically, the hydrophobic material may be wax, but is not limited thereto. When a sample is analyzed using the SERS substrate according to the present invention, the effective area that can be analyzed in a single performance is limited to an area of several millimeters in diameter where the light source is concentrated, due to the nature of the spectroscopic detection method. As such, since a sample spreads widely when the Raman-active area is formed to be wider than necessary, if the sample is used in the same amount, the amount of the analyte present per unit area is reduced and may thus make it difficult to detect the analyte present in a trace amount. Accordingly, to prevent the waste of a sample and improve the efficiency of detection, it may be desirable to form a Raman-active area in a limited region. In this regard, to prevent the metal nanoparticles from being coated on areas other than the designed Raman-active area, a method of blocking the interaction with the metal nanoparticles by impregnating or coating a hydrophobic material to the areas may be used. An example of the hydrophobic material to be used is wax. Considering that the substrate of the present invention is paper-based, a SERS-active area of a desired pattern may be formed by marking the Raman-active area on a paper substrate followed by waxing the remaining areas. For example, since paper can absorb wax, both sides of the paper can be blocked even when wax is applied to only one side thereof. The pattern formation by applying wax is merely an exemplary embodiment, and the scope of the present invention should not be limited thereto.

For example, the $1^{st}$ and $2^{nd}$ metals may be different from each other, and the $1^{st}$ and $2^{nd}$ metals may be each independently selected from the group consisting of gold, silver, platinum, aluminum, iron, zinc, copper, tin, bronze, brass, nickel, and alloys thereof. For example, any metal that can be uniformly distributed in the form of particles and exhibit the SERS effect can be used without limitation.

For example, a substrate comprising gold-silver composite bimetallic nanoparticles, which comprise both gold and silver by selecting silver as the $1^{st}$ metal and gold as the $2^{nd}$ metal or vice versa, may be prepared. Silver has an excellent SERS effect when used alone but has a disadvantage in that it is easily oxidized. On the other hand, gold has a slightly lower SERS effect than silver when used alone, but has excellent stability against oxidation.

Figure 19:
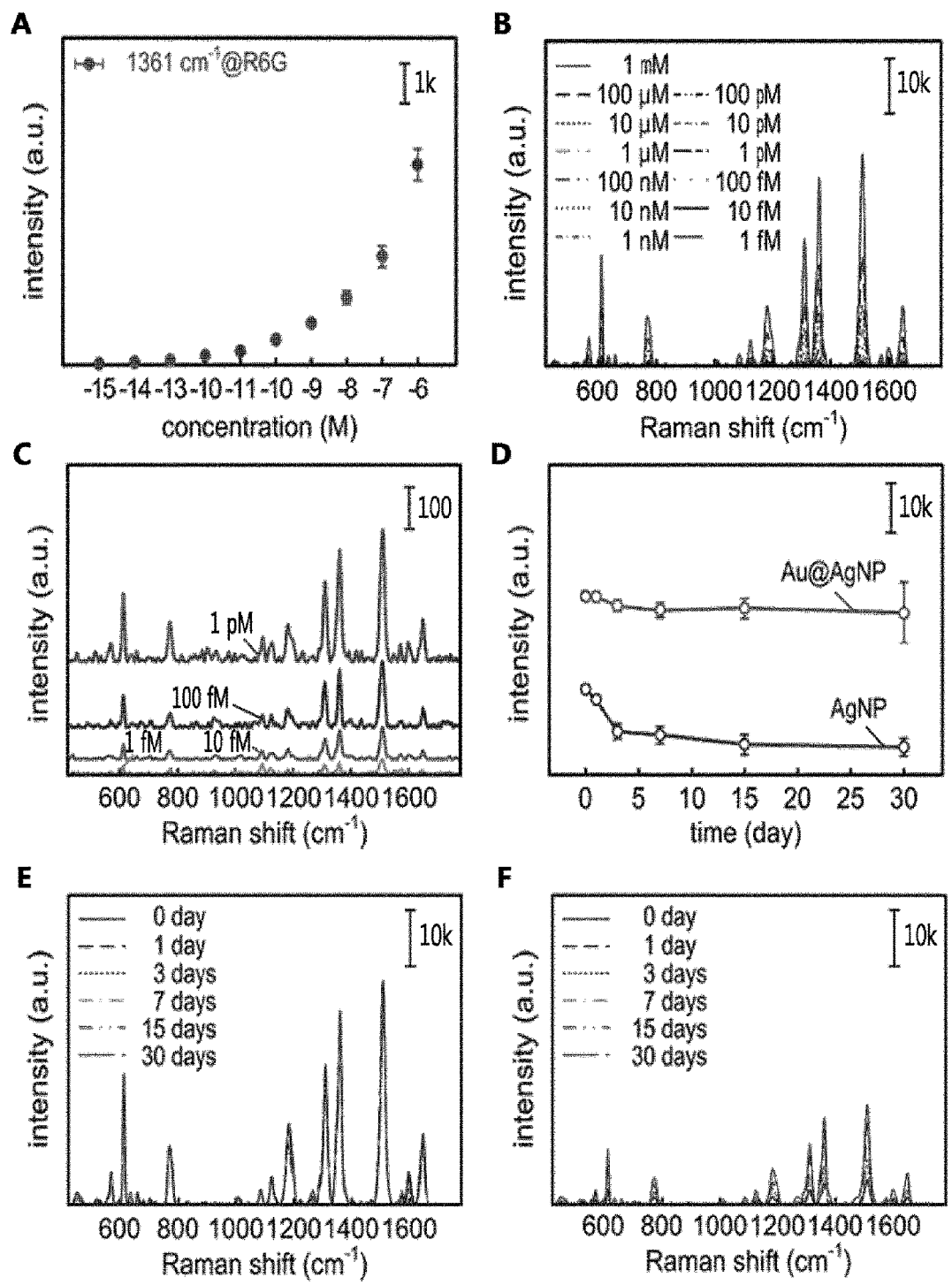
FIGS. 19A-F show the results with respect to the Raman signal enhancement effect of Rhodamine 6G (R6G), which is a SERS probe, on paper-based SERS substrates in which gold-silver composite bimetallic nanoparticles were introduced according to the continuous chemical reaction method; in which, (A) shows the Raman intensity at 1361 $cm^{-1}$ according to R6G concentration; (B) and (C) show concentration-dependent changes in Raman intensity; (D) shows a time-dependent decrease in Raman intensity by the oxidation of metal nanoparticles; (E) shows a time-dependent Raman spectrum of Au@AgNP; and (F) shows a time-dependent Raman spectrum of silver nanoparticles.

In a specific embodiment of the present invention, a substrate to which composite bimetallic nanoparticles are bound, in a form where silver nanoparticles are surrounded by gold, was prepared by sequentially performing the continuous chemical reaction method by selecting silver as the $1^{st}$ metal and gold as the $2^{nd}$ metal. In the case of a substrate comprising the composite bimetallic nanoparticles, it was confirmed that the substrate exhibited significantly improved stability against oxidation as well as an improved SERS effect compared to the substrate merely comprising silver nanoparticles, and thus the substrate showed almost no decrease in Raman intensity even after 30 days (FIG. 19).

For example, the precursor solutions of the $1^{st}$ metal and $2^{nd}$ metal may be different from each other, and may be aqueous solutions comprising the $1^{st}$ and $2^{nd}$ metals in an ionic state, respectively. Specifically, the precursor solutions of the $1^{st}$ metal and $2^{nd}$ metal may be each independently an aqueous solution of $HAuCl_4$, $NaAuCl_4$, or $AgNO_3$, but are not limited thereto.

The solutions of the $1^{st}$ reducing agent and $2^{nd}$ reducing agent comprising the reducing agents for the granulation by reducing metal ions, as metal precursors, adsorbed to the substrate are the same or different from each other, and these solutions may be an aqueous solution comprising sodium borohydride ($NaBH_4$), trioctylphosphine oxide (TOPO), sodium citrate, hexadecyltrimethylammonium chloride (HTAC), cetyltrimethylammonium bromide (CTAB), $NH_4OH$, or combinations thereof, but are not limited thereto.

For example, water may be used as the $1^{st}$ buffer, $1^{\prime th}$ buffer, $2^{nd}$ buffer, and $2^{\prime th}$ buffer, but these buffers are not limited to water. Any aqueous solution, which can remove metal precursors and/or metal nanoparticles which are loosely attached to the surface of a substrate, without modifying the metal precursors and/or reducing agents adsorbed on the substrate, reacting with them, or inhibiting the reactions with them, may be used without limitation.

The $1^{st}$ and/or $2^{nd}$ buffers may each be independently different depending on the kind of the metal. For example, an organic solvent such as ethanol, chloroform, etc., may be used, but the organic solvent is not limited thereto.

For example, steps (1) to (4) may be sequentially performed in one set, but these steps may be repeatedly performed in one or more sets. Specifically, the optimal conditions that can maximize the SERS effect may be explored by adjusting the size and density of the nanoparticles formed on a substrate and the thickness of the particle layer, by repeatedly performing the process of metal nanoparticle's forming-washing through adsorption-washing-reduction of the metal precursors.

Additionally, the paper-based SERS substrate according to the present invention may be prepared by a method which comprises: step (1) of preparing a solution of metal nanoparticles by mixing metal nanoparticles and an aqueous solution of carboxymethylcellulose; step (2) of preparing a paper substrate on which a desired pattern is formed; and step (3) of coating the solution of metal nanoparticles of step (1), on the paper substrate.

For example, the solution of metal nanoparticles may have a viscosity of 500 cP to 10,000 cP, more specifically, 700 cP to 9,000 cP, and even more specifically, 900 cP to 8,500 cP, but the viscosity is not limited thereto. For example, when the viscosity of the solution is lower than 500 cP, the viscosity is too low and thus non-uniform distribution of the metal nanoparticles may occur when the solution is coated on a paper substrate. Particularly, a coffee ring phenomenon, in which particles are mainly distributed at the edges of a pattern, may occur. In contrast, when the viscosity of the solution is greater than 10,000 cP, the solution becomes difficult to handle and a large portion of the solution may be wasted by remaining in unnecessary areas of a container or substrate.

For example, the metal nanoparticles to be used may have a uniform size with an average diameter of 10 nm to 100 nm, and more specifically, 10 nm to 50 nm. The metal nanoparticles may be used by purchasing those which are prepared by size and commercially available. Alternatively, those prepared using the method for preparing metal nanoparticles known in the art may be used. For example, gold nanoparticles may be prepared by citric acid capping based on the Turkevich method through chemical reduction from the precursor, $HAuCl_4$, but the preparation method is not limited thereto.

For example, the aqueous solution of carboxymethylcellulose may be used at a concentration of 0.7 wt % to 2.5 wt %, and more specifically 1 wt % to 2 wt %, but is not limited thereto. For example, when the concentration of the aqueous solution of carboxymethylcellulose is lower than 0.7 wt %, sufficient viscosity may not be provided when the metal nanoparticle solution is prepared by mixing carboxymethylcellulose solution with metal nanoparticles, and thus a non-uniform distribution of metal nanoparticles may occur when the metal nanoparticle solution is coated on a paper substrate. Due to the coffee ring phenomenon that occurs when the viscosity is low, as described above, the particles are mostly distributed on the interface where the pattern is formed, and due to the non-uniform distribution of particles, it may be difficult to provide reproducible results when performing analysis using the same. On the contrary, when the solution has a concentration greater than 2.5 wt %, it may be difficult to handle the solution and a large amount of the solution containing metal nanoparticles may remain in unnecessary areas of the container or substrate and may be wasted.

For example, the metal nanoparticle solution may be prepared by mixing metal nanoparticles and an aqueous solution of carboxymethylcellulose in a volume ratio of 1:5 to 1:10, more specifically, 1:5 to 1:8, and even more specifically, 1:6 to 1:8. In particular, the metal nanoparticles may be used in a concentrated state where most of the supernatant is removed after concentrating by centrifugation. For example, the centrifugation may be performed at 5000 rpm to 8000 rpm for 5 to 15 minutes, but is not limited thereto. Alternatively, when a non-concentrated metal nanoparticle dispersion is used, the concentration and/or the mixing volume ratio of then aqueous solution of carboxymethylcellulose may be adjusted in consideration of the volume ratio.

Meanwhile, step (2), which is a step of preparing a paper substrate, may be carried out by coating with wax the areas of the paper substrate, excluding the pattern of the paper substrate where the desired pattern is designed, but is not limited thereto. When a sample is analyzed using the SERS substrate according to the present invention, the effective area that can be analyzed in a single performance is limited to an area of several millimeters in diameter where the light source is concentrated, due to the nature of the spectroscopic detection method. As such, since a sample spreads widely when the Raman-active area is formed to be wider than necessary, if the sample is used in the same amount, the amount of the analyte present per unit area is reduced and may thus make it difficult to detect the analyte present in a trace amount. Accordingly, to prevent the waste of a sample and improve the efficiency of detection, it may be desirable to form a Raman-active area in a limited region. In this regard, to prevent the metal nanoparticles from being coated on areas other than the designed Raman-active area, a method of blocking the interaction with the metal nanoparticles by impregnating or coating a hydrophobic material to the areas may be used. An example of the hydrophobic material to be used is wax. Considering that the substrate of the present invention is paper-based, step (2) may be formed by marking the Raman-active area on a paper substrate followed by waxing the remaining areas. Since paper can absorb wax, both sides of the paper can be blocked even when wax is applied to only one side thereof. The pattern formation by applying wax is merely an exemplary embodiment, and the scope of the present invention should not be limited thereto.

Additionally, the method may further comprise step (4) of drying by heating after step (3) of coating the solution of metal nanoparticles. The coating and/or drying may be performed using any method known in the art without limitation. The coating may be performed by applying solution droplets to the area to be coated followed by a uniform spreading with a blade, but is not limited thereto. The step of drying by heating may be performed by maintaining the temperature at 40° C. to 60° C. for 100 to 200 seconds using a hot plate, but is not limited thereto. Specifically, the drying may be completed within a short time of less than 5 minutes, more specifically less than 3 minutes, and even more specifically less than 2 minutes, so that the metal nanoparticles in the solution can be blocked from spreading out to the edge and are thereby uniformly distributed within a desired area.

For example, steps (3) and (4) of coating and drying the metal nanoparticle solution may be performed once or may be repeatedly performed 2 to 5 times. Generally, metal nanoparticles which are uniformly distributed by being spaced at regular intervals can induce SERS. Additionally, the SERS degree can be maximized by adjusting the space between the metal nanoparticles. Specifically, in the method for preparing a SERS substrate according to the present invention, the space between metal nanoparticles can be reduced while the number of particles present in a given area is constantly increased by repeatedly performing the process of coating the metal nanoparticle solution at a predetermined concentration.

Specifically, it is preferred that the step of coating the metal nanoparticle solution may be repeatedly performed a total of 1 to 5 times, and more preferably, be repeatedly performed 2 to 3 times. For example, in the case of repeatedly performing 5 times or more, the space between metal nanoparticles becomes narrowed more than necessary, which may actually reduce the signal or may interfere with each other and shift the wavelength. However, the number of repetitions may be adjusted by the concentration of the metal nanoparticles, i.e., the mixing ratio between the metal nanoparticles and an aqueous solution of carboxymethylcellulose in the metal nanoparticle solution.

DETAILED DESCRIPTION OF THE INVENTION

Hereinafter, the present invention will be described in more detail with reference to the following Examples.

However, these Examples are for illustrative purposes only and the invention is not limited by these Examples.

<Reagents and Materials>

Hydrogen tetrachloroaurate (HAuCl$_4$, >99%), trisodium citrate dehydrate (99%), sodium carboxymethylcellulose (CMC), and Rhodamine B (RhB, >95%) were purchased from Sigma Aldrich (St. Louis, Mo., USA). All of the reagents were of analytical grade and all of the solutions were prepared using distilled water (18.3 MΩ·cm). Whatman cellulose chromatography paper (grade 1) with a thickness of 0.18 mm and a linear flow rate of 72.22 μm/sec was purchased from Sigma-Aldrich.

<Instruments>

The size and shape of gold nanoparticles (AuNPs) were confirmed using the JEM-2100F field emission transmission electron microscope (FE-TEM, JEOL, Tokyo, Japan) operated at 200 kV acceleration voltage. The UV-Vis absorption spectrum of the colloidal AuNPs was measured using the CARY 300 UV-Vis spectrophotometer (Agilent, Santa Clara, Calif., USA) using 1 cm quartz cells. The viscosity of the CMC solution was measured at room temperature using the DV-II+ Pro viscometer (Brookfield, Middleboro, Mass., USA).

The morphological characteristics of the paper substrate coated with CMC-AuNPs according to the present invention were confirmed using the S-4700 field emission transmission electron microscope (FE-SEM; Hitachi, Tokyo, Japan) at 5 kV acceleration voltage. The elementary composition of the synthesized product was confirmed using the 7200-H energy-dispersive X-ray spectrometer (EDX; HORIBA, Northampton, England).

Raman spectrum was obtained using the SENTERRA confocal Raman system (Bruker Optics, Billerica, Mass., USA). A 785 nm diode laser light source with 10 mW power was focused to a spot size of about 2.4 μm with 20× objective lens (NA=0.4). The spectrum at each point was recorded at a spectral resolution of 5 cm$^{-1}$ in a range of 417 cm$^{-1}$ to 1782 cm$^{-1}$. The spectrum was recorded twice at room temperature for 30 seconds of collection time. The reliability was confirmed by measuring the Raman spectrum of each sample at 10 random printed spots on the SERS-active area. Raman spectra were evaluated using 2 μL analytic droplets.

Example 1: Preparation of CMC-AuNPs Ink

AuNPs were obtained by citric acid capping based on the Turkevich method by chemical reduction. 38.8 mM trisodium citrate dehydrate (1 mL) was added to 1 mM HAuCl$_4$ (10 mL) and heated on a hot plate at 90° C. for 20 minutes with magnetic stirring. The color of the solution changed from light yellow to dark purple. The reaction flask was then immediately removed from the hot plate. Stirring was maintained until the solution was cooled to room temperature.

To prepare screen printing inks, colloidal AuNP (1 mL) was concentrated by centrifugation at 6000 rpm for 10 minutes and 99% of the supernatant was removed. The concentrated AuNPs were dispersed in distilled water along with sodium CMC. The optimum stencil ink was achieved by controlling the concentration of CMC and the ratio of AuNPs.

Example 2: Preparation of SERS Platform

A SERS paper platform was prepared to include two areas, a SERS-active area and a labeling area. A paper (8×20 mm$^2$) on which 2 mm hydrophilic circular area and a labeled area designed by Autodesk (San Rafael, Calif., USA) were printed by the Xerox ColorQube 8570N printer (Fuji Xerox, Tokyo, Japan) are shown in FIG. 1A. Wax was uniformly impregnated in the drying oven at 130° C. for 45 seconds in the areas excluding the SERS-active area and the labeling area of the paper, and dried at room temperature.

A stencil cut-out hole (diameter: 3 mm; and thickness: 180 μm) was adjusted. Since the hydrophilic SERS-active area has a diameter of 2 mm, the size of the stencil cut-out hole was designed to be larger so as to obtain uniform SERS signals. This was attributed to the coffee ring effect due to the outwardly-directed surface tension acting on the interface between the ink and a side of the mask wall, which is the area of the hydrophobic wax (FIG. 1B). CMC-AuNPs ink (4 μL) was added dropwise to the stencil hole and the blade was moved across the stencil. The resultant was dried on a hot plate at 50° C. for 120 seconds (once). The CMC-AuNPs ink was printed on a paper impregnated with wax and the SERS-functionalized substrate was photographed and is shown in FIG. 1C.

Experimental Example 1: Characterization of AuNPs

The characteristics of citric acid-capped AuNPs were analyzed by TEM images and UV-Vis spectra (FIGS. 2A-D). As shown in the FE-TEM images, AuNPs exhibited stable monodispersity with an average diameter of 25±8 nm. The UV-Vis spectrum of the AuNP colloids had a maximum absorption wavelength ($\lambda_0$) of 525 nm. Generally, the size of particles in the range of 25 nm to 100 nm is determined by the following equation;

$$\lambda_{max} - \lambda_0 = L_1 \exp(L_2 d) \qquad (1)$$

where $\lambda_0$ represents the maximum absorption wavelength, $\lambda_{max}$ represents the maximum value of $\lambda_0$, and d represents the particle size ($L_1$=6.53 and $L_2$=2.16×10$^{-2}$ are set as constants from the experimental plot). The calculated average particle size was 31.9 nm when the peak wavelength of AuNPs was 525 nm (FIG. 2C). The AuNPs were slightly agglomerated in the colloids, but the calculated particle size was within the range of the particle size measured by TEM. The size of AuNPs is one of the important factors that determine SERS improvement.

Experimental Example 2: Viscosity of CMC Solutions

Since direct printing of concentrated AuNPs colloids alone is not suitable for uniform dispersion due to low viscosity, AuNPs were added to the CMC solution, which is a conventional viscous reagent that is water-soluble and has a different viscosity depending on the concentration, so as to control the viscosity of the printing ink to a suitable range. Since CMC has a much higher viscosity than water, it was expected to have an important role in supporting AuNPs to be uniform on a paper substrate. The viscosity of the CMC solutions at 4 different concentrations were measured with a viscometer. The viscosity of CMC increased exponentially with increasing concentration (FIG. 2D). The 0.5 wt % CMC solution was too low in viscosity to cause non-uniform dispersion of AuNPs on the paper substrate while the 3 wt % CMC solution was too viscous to handle in the process of producing the ink (FIGS. 3A-C). Meanwhile, both 1 wt % and 2 wt % CMC solutions were shown to be suitable for uniform distribution and attachment of AuNPs on the paper substrate. Additionally, the high surface roughness of the paper substrate provided a synergistic effect so that the CMC solutions can act as an adhesive. The 1 wt % and 2 wt % CMC concentrations were selected as major conditions of the screen printing ink.

Experimental Example 3: Surface of CMC-AuNPs Ink-Printed Paper

The shapes of CMC-AuNPs printed on a paper substrate were observed by SEM and the images obtained are shown in FIGS. 4A-B. The presence of cellulosic fibers not aligned was observed (FIG. 4A), and the porous structure between the cellulose fibers was filled with a sodium CMC solution which exhibited viscosity (FIG. 4B), unlike the bare paper or wax-impregnated paper (FIGS. 5A-B). AuNPs were well-distributed on the cellulose fibers within a range of 2.4 μm focal spot size capable of measuring the Raman spectrum (FIG. 4B). The blurred SEM image of the surface of CMC-AuNPs-printed paper was due to the mixing with sodium CMC. Then, EDX-based observation of the molecules relative to the composition of these particles was performed so as to determine whether or not these particles were AuNPs (FIG. 6). The EDX mapping finding results showed that CMC-AuNPs-loaded paper can be used as a SERS substrate.

Experimental Example 4: Effects Depending on Mixing Ratio Between AuNPs and CMC Solution To confirm the change of Raman signal intensity according to the ratio of AuNPs to a CMC solution, 2 μL of 1 mM RhB (a probe molecule for Raman spectroscopy) was added dropwise to the SERS-active area to explore the conditions of the CMC-AuNPs ink. The predominant Raman peaks of RhB appeared at 620 cm$^{-1}$ (an aromatic bending), 1201 cm$^{-1}$ (an aromatic C—H bending), and 1356 cm$^{-1}$ (an aromatic C—C stretching), and the remarkable Raman peak at 1356 cm$^{-1}$ was selected as the reference peak for RhB analysis.

Figure 7:
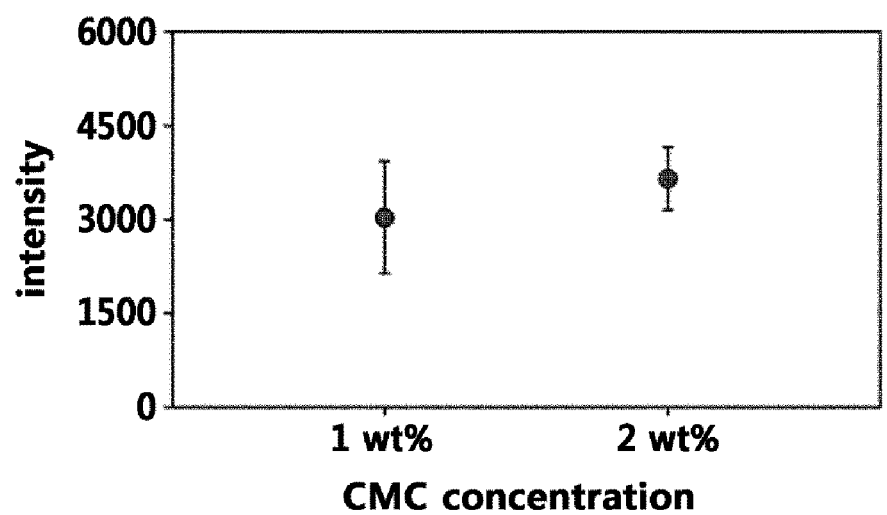
FIG. 7 shows the Raman intensity measured at the 1356 $cm^{-1}$ band according to CMC concentration (1 wt % and 2 wt %, respectively) upon 3 times of printing with the CMC-AuNPs ink (CMC:AuNPs=5:1).

The optimal CMC concentration exhibiting the maximum Raman intensity was assayed at 1 wt % and 2 wt % CMC concentrations. An ink solution having a 5:1 volume ratio of CMC solution to AuNPs (CMC:AuNPs=5:1) was prepared using the CMC solution at these two concentrations. The Raman signals thereof were measured on a substrate where the CMC-AuNPs ink was repeatedly printed 3 times, and the intensity thereof is shown in FIG. 7. As shown in FIG. 7, the combination with the 2 wt % CMC solution showed a superior SERS signal and lower spectral deviation compared to the 1 wt % CMC solution. This may be due to the higher viscosity of the CMC solution which inhibits the tension to move out and accommodates the AuNPs (FIGS. 3A-C). Additionally, the rapid drying of CMC-AuNPs at 50° C., while repeatedly performing the printing, prevented the spreading of the AuNPs to the edge and induced the AuNPs to be well-distributed in the SERS-active area. Accordingly, the 2 wt % CMC-AuNP was selected as the optimal combination for a printing ink.

Figure 8:
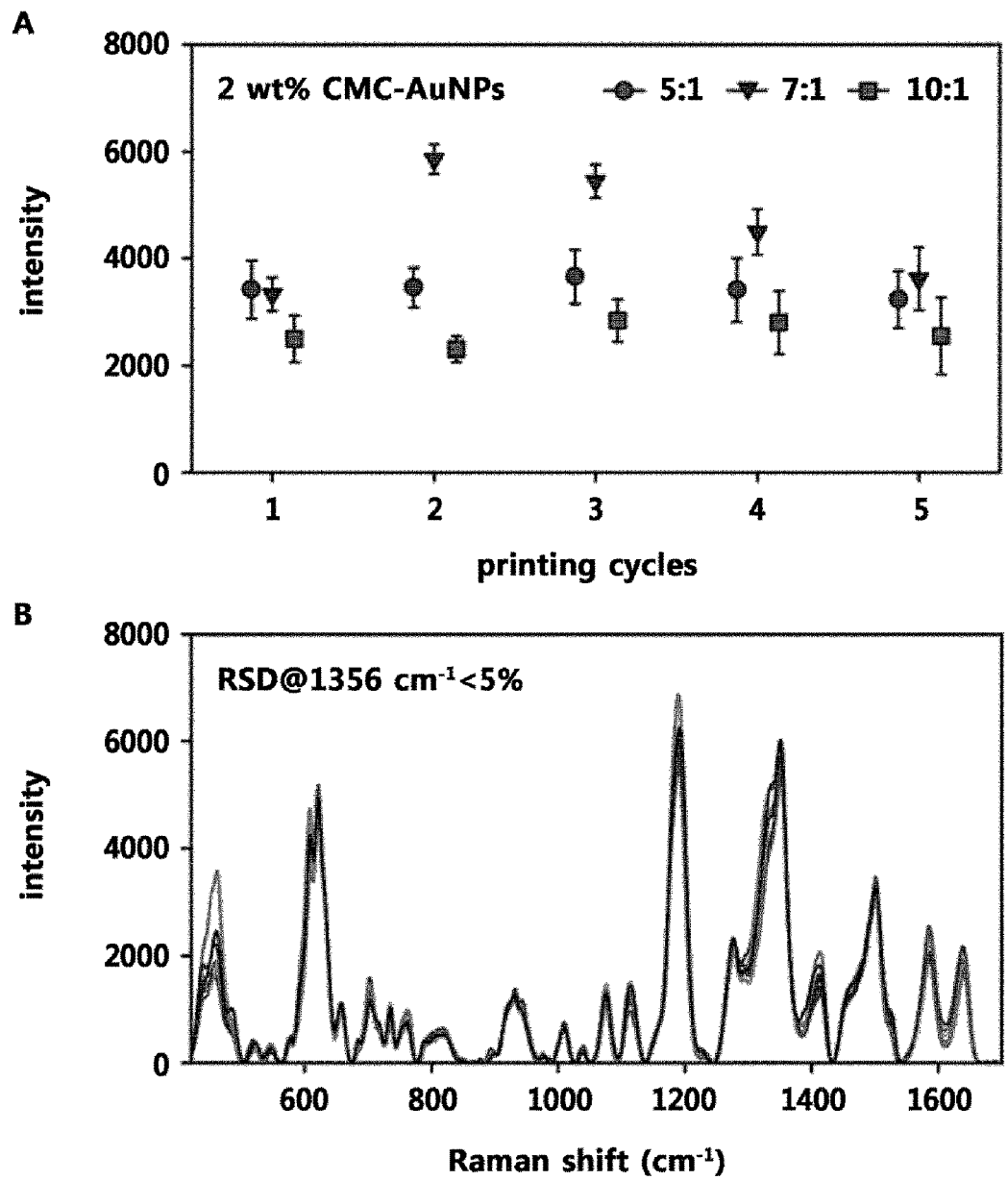
FIGS. 8A-B show the optimization results of the CMC-AuNPs ink; in which (A) shows the Raman intensity according to the number of printings of the CMC-AuNPs ink solution in which the CMC solution and AuNPs were mixed at three different volume ratios of 5:1, 7:1, and 10:1; and (B) shows the high reproducibility of the 2 wt % CMC-AuNPs ink solution (CMC:AuNPs=7:1) (RSD: relative standard deviation).

Then, the effect of the amount of the AuNPs on Raman intensity was confirmed by varying the volume ratio of the AuNPs in the screen printing ink solution. For this purpose, the 2 wt % CMC solution was mixed with the AuNPs in the following three volume ratios: the volume ratios of the CMC solution to the AuNPs are 5:1, 7:1, and 10:1, respectively. The Raman intensity of the CMC-AuNPs ink solution prepared at the three different volume ratios was measured according to the number of printings and the results are shown in FIG. 8A. Among them, the 7:1 CMC-AuNPs ink solution showed a superior SERS effect compared to the solution prepared at different volume ratios. The maximum SERS intensity was observed when the solution of the corresponding volume ratio was printed twice. Basically, the resonance of NPs at the surface of a paper is caused by the incident energy into the nanometer space of several nanometers between the particles. The reflected energy is amplified by scattering due to resonance, and this energy can exert a significant effect on SERS. The space between particles is affected by the number of particles. When the size of the nanoparticles is constant and the number of particles increases in a limited area, the distance between particles decreases and Raman scattering increases. However, when the number of particles increases excessively, AuNPs would have the properties of a film rather than individual particles. Accordingly, the resonance of NPs weakens and the Raman intensity decreases. The results of the present invention were also consistent with this phenomenon; when the printing was repeated twice, the SERS intensity was doubled as compared to a single printing. However, additional repeated printing on a paper substrate resulted in a decrease of SERS intensity and a larger deviation of the Raman peak. To confirm the reliability of the SERS spectra, SERS spectra were arbitrarily measured at 10 different positions in the SERS-active area of a paper substrate prepared by repeatedly performing the printing twice with the optimized 7:1 CMC-AuNPs ink solution. The average intensity and deviation of the point-to-point of the SERS peak at 1356 cm$^{-1}$ was 5,858±279 (Table 1) and the corresponding relative standard deviation (RSD) was 4.77%. The intensity of the SERS signal was controlled by the SERS effect, laser light source focusing, biological samples, and three or four other variables. Although the Raman intensity varied between detection sites, the overall variance of less than 5% represents high reproducibility of the SERS technique. Therefore, the noise-dependence, uniformity, and reproducibility of the SERS spectroscopic signal support that the proposed method could be a highly sensitive and selective assay method for biological fluids.

TABLE 1

2 wt % CMC:AuNPs Ink

| Volume Ratio | Number of Printing | Raman Intensity | | |
|---|---|---|---|---|
| | | Mean | SD | RSD @1356 cm$^{-1}$ (%) |
| CMC:AuNPs (5:1) | 1 | 3416.7 | 540.4 | 15.82 |
| | 2 | 3456.4 | 366.4 | 10.60 |
| | 3 | 3655.8 | 505.5 | 13.83 |
| | 4 | 3409.3 | 590.8 | 17.33 |
| | 5 | 3233.0 | 529.3 | 16.37 |
| CMC:AuNPs (7:1) | 1 | 3331.7 | 310.3 | 9.31 |
| | 2 | 5858.4 | 279.4 | 4.77 |
| | 3 | 5442.7 | 313.4 | 5.76 |
| | 4 | 4492.1 | 421.0 | 9.37 |
| | 5 | 3619.2 | 587.9 | 16.24 |
| CMC:AuNPs (10:1) | 1 | 2501.3 | 434.3 | 17.36 |
| | 2 | 2310.5 | 241.2 | 10.44 |
| | 3 | 2840.4 | 395.6 | 13.93 |
| | 4 | 2804.8 | 583.9 | 20.82 |
| | 5 | 2553.8 | 718.6 | 28.14 |

*Standard Deviation (SD), Relative Standard Deviation (RSD)

Figure 9:
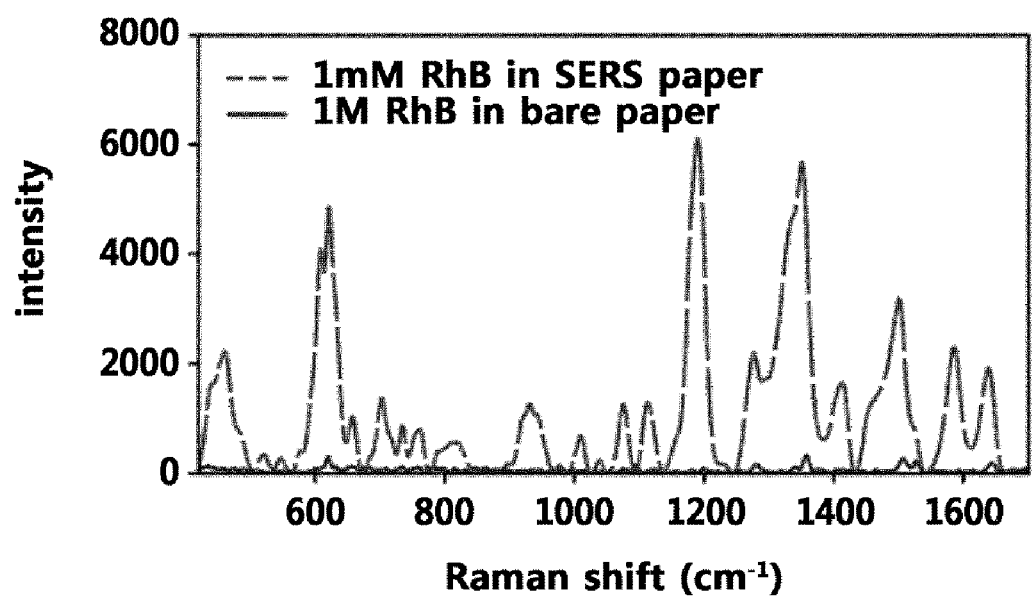
FIG. 9 shows the results of the Raman spectra of RhB at 1 mM and 1 M concentrations on a SERS-active paper (coated with the CMC-AuNPs ink) and a bare paper.

Experimental Example 5: Quantitative Comparison of SERS Activity of CMC-AuNPs Ink Printed Paper To quantify the SERS activity of screen printing inks, Raman spectra of a SERS paper printed with a CMC-AuNPs ink and an untreated bare paper were measured using 1 mM RhB and 1 M RhB, and the results are shown in FIG. 9. The Raman intensity in the 1356 cm$^{-1}$ band of 1 mM RhB on the SERS paper (5,858) was about 18 times higher compared to the measured value for 1 M RhB on the bare paper (328). Accordingly, the enhancement factor (EF) was calculated from the difference in Raman intensity between two different substrates by the following equation:

$$EF = \left(\frac{I_{SERS}}{I_{bare}}\right)\left(\frac{N_{bare}}{N_{SERS}}\right) \quad (2)$$

In the above equation, $I_{SERS}$ and $I_{bare}$ each represent the Raman intensity of the molecules measured on the SERS paper, and the bare paper and $N_{SERS}$ and $N_{bare}$ each represent the average number of molecules adsorbed within the scattering volume for the SERS and non-SERS areas. Assuming a uniform distribution of probe molecules on the substrate, the number of adsorbed molecules can be calculated as follows:

$$N = \left(N_A \cdot c \cdot \frac{V_{droplet}}{A_{spot}}\right) A_{laser} \quad (3)$$

In the above equation, $N_A$ represents the Avogadro constant, c represents the concentration of the probe molecules, V represents the volume of the molecular droplets, $A_{spot}$ represents the size of the substrate, and $A_{laser}$ represents the size of the laser spot. Since the same method was applied to two substrates for the assay of Raman measurements, variables of RhB relating to the $N_A$, V, $A_{spot}$, and $A_{laser}$ were the same with each other. Accordingly, the equation (2) can be written as follows:

$$EF = \left(\frac{I_{SERS}}{I_{bare}}\right)\left(\frac{c_{bare}}{c_{SERS}}\right) \quad (4)$$

In the above equation, $c_{SERS}$ and $c_{bare}$ represent the RhB concentration on a SERS paper and a bare paper, respectively. The final EF at 1356 cm$^{-1}$ was $1.8 \times 10^4$. The EF value represents the presence of SERS activity on a paper printed with the CMC-AuNPs ink.

Experimental Example 6: Application to Biomaterial Analysis

A tear sample was added to the SERS substrate of the present invention and the Raman spectrum was measured to analyze the presence of virus infection. The analysis of the obtained Raman spectra was performed by the method disclosed earlier in the journal article by the present inventors (*Anal. Chem.*, 2014, 86 (22): 11093 to 11099). Specifically, when the measured Raman spectra were normalized relative to the peak at 1003 cm$^{-1}$, no shift of Raman peaks was observed between tears collected from normal persons and those from virus-infected patients, but the ratios of Raman peaks were shown to vary at 1242 cm$^{-1}$ and 1342 cm$^{-1}$. Accordingly, it was possible to confirm the virus infection from the tear samples by comparing the values derived from the following equation:

$$\delta_{VIRUS} = \frac{I_{1342}}{I_{1242}}$$

The $I_{1242}$ and $I_{1342}$ correspond to the Raman intensity of the peaks corresponding to amide III-sheet and C—H modification, respectively.

Figure 10:
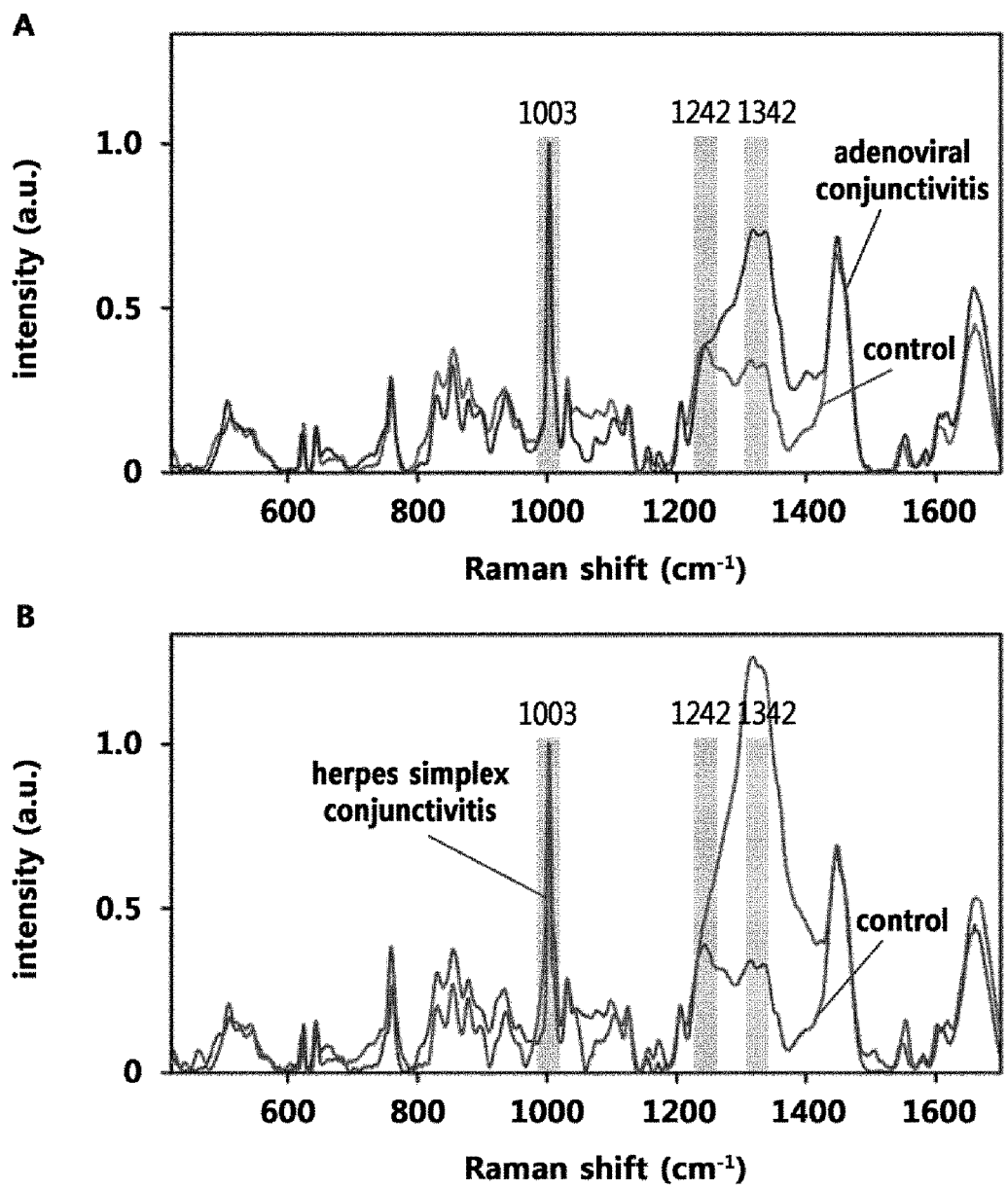
FIGS. 10A-B show the results of the Raman spectra measured by applying tear samples, collected from a normal person and a patient with viral infectious conjunctivitis, to the paper substrate of the present invention; in which (A) and (B) show the Raman spectra of tear samples from patients with adenoviral conjunctivitis and herpes simplex conjunctivitis, respectively.
Figure 11:
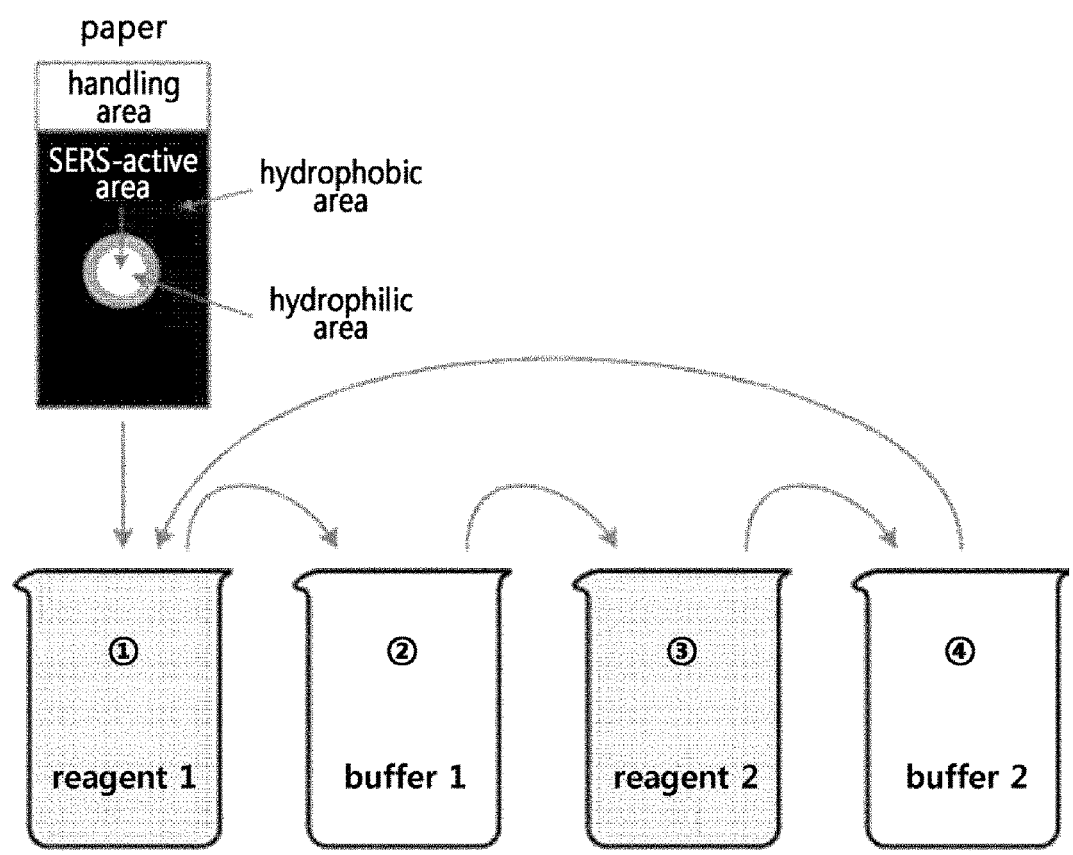
FIG. 11 shows a schematic diagram illustrating a method for preparing a paper-based SERS substrate using a continuous chemical reaction method according to the present invention.

Tear samples were collected from a normal person and a patient with conjunctivitis caused by adenovirus infection or herpes simplex infection, respectively, and applied to the SERS substrate of the present invention to measure the Raman spectrum (FIGS. 10A-B), and the $\delta_{VIRUS}$ values were derived using the above equation. As a result, the $\delta_{VIRUS}$ value derived from the Raman spectrum measured from the tear of the patient with adenoviral conjunctivitis was 1.87, and the $\delta_{VIRUS}$ value derived from the Raman spectrum measured from the tear of the patient with herpes simplex conjunctivitis was significantly increased to 2.47, whereas the $\delta_{VIRUS}$ value derived from the Raman spectrum measured from the tear of the normal person was 0.80. The experiment was repeatedly performed in a plurality of patients and it was confirmed that the results were reproducible. These results indicate that the $\delta_{VIRUS}$ can be served as a marker for diagnosing conjunctivitis induced by viral infection. That is, when the $\delta_{VIRUS}$ value derived from the Raman spectrum measured from the tear of a patient being suspected of having viral infectious conjunctivitis is greater than 1, the patient can be determined as a conjunctivitis patient due to viral infection, and additionally, when the $\delta_{VIRUS}$ value is greater than 2, the conjunctivitis can be determined to be due to the infection of herpes simplex virus.

Example 3: Preparation of Paper-Based SERS Substrate, on which Gold Nanoparticles are Adsorbed, Using Continuous Chemical Reaction Method (Successive Ionic Layer Adsorption and Reaction; SILAR)

A 10 mM aqueous solution of HAuCl$_4$ (10 mL) as a precursor solution of gold and a 10 mM aqueous solution of NaBH$_4$ (10 mL) as a solution of a reducing agent were prepared. Distilled water was used as a buffer for washing. The precursor solution of gold and the solution of a reducing agent were prepared in separate beakers, and distilled water for washing was also prepared in two beakers.

The SERS-active area was marked by drawing a 2 mm-diameter circle on a filter paper (8 mm×20 mm), followed by smearing the external area except the internal area of the circle with wax, treated in a drying oven at 130° C. for 45 seconds for uniform impregnation of the wax thereinto, and dried at room temperature. The filter paper impregnated with the wax was immersed in the precursor solution of gold prepared in advance and left therein for 30 seconds to allow the gold ions to be adsorbed to a paper substrate. The filter paper was removed from the precursor solution of gold and immersed into a first beaker with distilled water and washed. The paper substrate which was immersed and washed in distilled water was withdrawn from that beaker and immersed into a beaker containing a solution of a reducing agent and left therein for 30 seconds to allow gold nanoparticles to grow from the gold ions adsorbed to the paper substrate. Upon completion of the reaction, the paper substrate on which gold nanoparticles were formed was withdrawn from the solution of a reducing agent and immersed into a second beaker with distilled water for washing. In the series of steps above, the levels of the solutions were adjusted so that the previously indicated SERS-active area could be sufficiently immersed into the solution. The series of steps above as one cycle were repeatedly performed five times.

Example 4: Preparation of Paper-Based SERS Substrate on which Silver Nanoparticles are Adsorbed Using Continuous Chemical Reaction Method A paper-based SERS substrate, on which silver nanoparticles were adsorbed instead of gold nanoparticles, was prepared by performing the continuous chemical reaction method in the same manner as in Example 3, except that an aqueous solution of $AgNO_3$ (10 mL) was used as a precursor solution of metal instead of an aqueous solution of $HAuCl_4$, a precursor solution of gold. The number of repetitions was increased to 5 times, 10 times, 15 times, and 20 times to produce four different types of substrates, respectively.

Comparative Example 1: Preparation of Aluminum-Foil-Based SERS Substrate on which Gold Nanoparticles are Adsorbed Using Continuous Chemical Reaction Method An aluminum foil-based SERS substrate, on which gold nanoparticles were adsorbed, was prepared using the same reagent and method as in Example 3, except that aluminum foil was used instead of the filter paper as a substrate.

Comparative Example 2: Preparation of Glass-Based SERS Substrate on which Gold Nanoparticles are Adsorbed Using Continuous Chemical Reaction Method A glass-based SERS substrate, on which gold nanoparticles were adsorbed, was prepared using the same reagent and method as in Example 3, except that a glass substrate was used instead of the filter paper as a substrate.

Comparative Example 3: Preparation of PET-Film-Based SERS Substrate on which Gold Nanoparticles are Adsorbed Using Continuous Chemical Reaction Method A PET-film-based SERS substrate, on which gold nanoparticles were adsorbed, was prepared using the same reagent and method as in Example 3, except that a PET film was used instead of the filter paper as a substrate.

Comparative Example 4: Preparation of Paper-Based SERS Substrate on which Gold Nanoparticles are Adsorbed Using Mixed Solution of Carboxymethylcellulose and Gold Nanoparticles First, a CMC-AuNPs ink for screen printing comprising gold nanoparticles and carboxymethylcellulose (CMC) was prepared. Specifically, 38.8 mM trisodium citrate dehydrate (1 mL) was added to 1 mM $HAuCl_4$ (10 mL) and heated on a hot plate at 90° C. for 20 minutes with magnetic stirring. The color of the solution changed from light yellow to dark purple. Then, the heating was immediately stopped and stirring was maintained until the solution was cooled to room temperature.

1 mL of the thus obtained colloidal AuNP was taken and concentrated at 6000 rpm for 10 minutes, and 99% of the supernatant was removed. The concentrated AuNPs were mixed with an aqueous solution of 2 wt % sodium CMC in a 1:7 volume ratio to prepare the CMC-AuNPs ink.

A stencil cut-out hole with a 3 mm diameter and a 180 μm thickness was aligned on the filter paper, which was prepared by wax treatment in the same manner as in Example 3, by adjusting so as to have the same center as the pre-marked surface-enhanced Raman-active area with a 2 mm diameter. CMC-AuNPs ink (4 μL) was added dropwise to the stencil hole, coated by moving the blade across the stencil and was dried on a hot plate at 50° C. for 120 seconds. The process of coating and drying CMC-AuNPs ink was repeated additionally.

Experimental Example 7: Absorptivity of Gold Nanoparticles According to Type of Substrate when Applying Continuous Chemical Reaction Method Gold nanoparticles were formed according to Example 3 and Comparative Examples 1 to 3 by applying the continuous chemical reaction method using paper, aluminum foil, glass, and a PET film as a substrate, respectively. The external shapes and structures of the microscopic surfaces of the finally-prepared substrates were observed by the naked eye and in a 20× optical microscope, respectively. The results are shown in FIG. 12.

As shown in FIG. 12, it was confirmed that the gold nanoparticles were uniformly distributed over the surface when a paper was used as a substrate, whereas the gold nanoparticles were non-uniformly distributed when aluminum foil or glass was used as a substrate, and gold nanoparticles were not attached at all when a PET film was used as a substrate.

Figure 13:
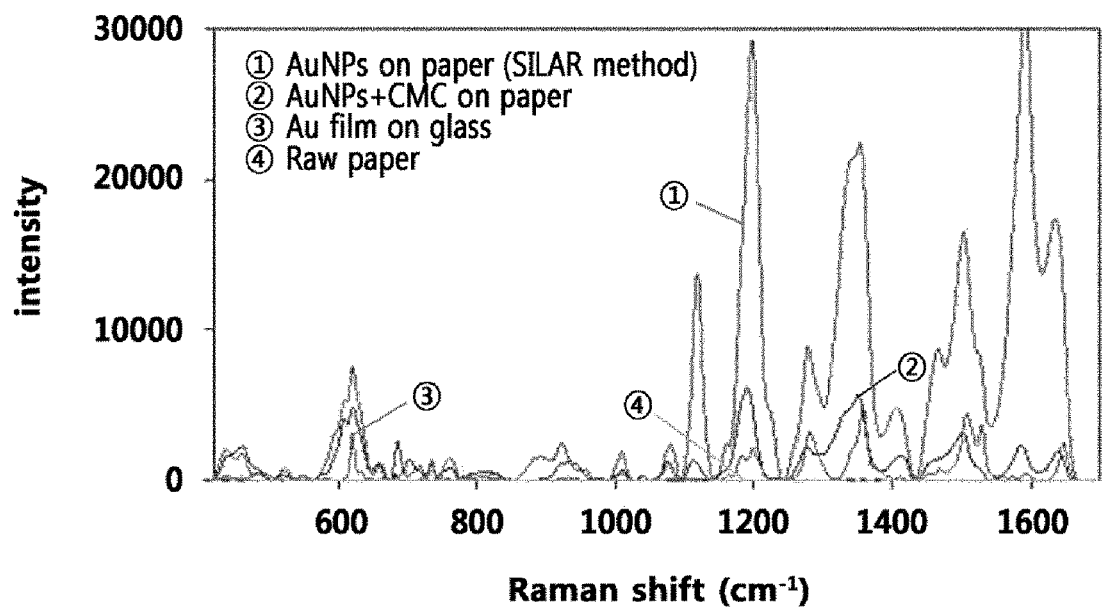
FIG. 13 shows the intensity of signals for the Raman shift of Rhodamine B (RhB) on substrates prepared by different methods. For the substrates, a paper-based substrate comprising gold nanoparticles prepared by applying the continuous chemical reaction method, a paper-based substrate prepared by screen printing using an ink comprising carboxymethylcellulose and gold nanoparticles, thin gold film formed on glass, and a paper substrate without any treatment were used.

Experimental Example 8: Change in Raman Intensity of Raman-Active Molecules According to Type and Preparation Method of Substrates Paper-substrates comprising gold nanoparticles prepared according to Example 3 and Comparative Example 4, thin gold film, and untreated paper were treated with Rhodamine B (RhB), which is a Raman-active molecule, at a concentration of 1 mM and Raman spectra were measured therefrom. From the measurements, a graph of the intensity for Raman shift was derived and the results are shown in FIG. 13, and the intensities at three different Raman shift wavelengths (620 $cm^{-1}$, 1201 $cm^{-1}$, and 1356 $cm^{-1}$), which are the main peaks of RhB among the peaks of the graphs, are summarized in Table 2 below.

Specifically, the Raman spectra were obtained using the SENTERRA confocal Raman system (Bruker Optics, Billerica, Mass., USA). A 785 nm diode laser light source with 10 mW power was focused to a spot size of about 2.4 μm with 20× objective lens (NA=0.4). The spectrum at each point was recorded at a spectral resolution of 5 $cm^{-1}$ in a range of 417 $cm^{-1}$ to 1782 $cm^{-1}$. The spectrum was recorded twice at room temperature for 30 seconds of collection time. The reliability was confirmed by measuring the Raman spectrum of each sample at 10 random printed spots on the SERS-active area to confirm reliability. Raman spectra were evaluated using 1 mM RhB of 2 μL analytic droplets as a sample.

TABLE 2

| Raman Peaks of RhB | SILAR (Example 1) | AuNPs + CMC (Comparative Example 4) | Au Film | Bare Paper |
|---|---|---|---|---|
| 620 cm$^{-1}$ | 7533 | 4868 | 3186 | 45 |
| 1201 cm$^{-1}$ | 29328 | 6120 | 2103 | 31 |
| 1356 cm$^{-1}$ | 22383 | 5680 | 4945 | 75 |

As shown in FIG. 13 and Table 2, with respect to the Raman-active molecule coated on the paper substrate without any treatment, it was difficult to detect the signal even at the peak positions. In contrast, it was possible to detect Raman signals with a significantly-increased intensity by the Raman signal enhancement effect of the corresponding substrate on the paper substrates comprising gold nanoparticles (Example 3 and Comparative Example 4) or thin gold film. In particular, when the substrate of Example 3 was used, the intensity was shown to have 1.5 to 4.8 times higher intensity compared to when that of Comparative Example 4 prepared by screen printing was used, and 2.4 to 13.9 times higher intensity Raman signals compared to when the thin gold film was used, according to the wavenumber. This suggests that when the appropriate wavenumber is selected, the detection using the substrate of the present invention enables about 14 times higher sensitivity compared to when the thin gold film is used as a substrate.

Experimental Example 9: Change in Raman Intensity of Raman-Active Molecules According to Type of Substrates In a SERS substrate in which gold nanoparticles were distributed on the surface thereof prepared by the continuous chemical reaction method, in order to confirm the difference of the SERS effect according to the material of the basic substrate, paper, aluminum foil, glass, and a PET film, which comprise gold nanoparticles prepared according to Example 3 and Comparative Examples 1 to 3, respectively, were coated with RhB at a concentration of 1 mM, and the Raman spectra were measured. The results are shown in FIG. 14.

Figure 14:
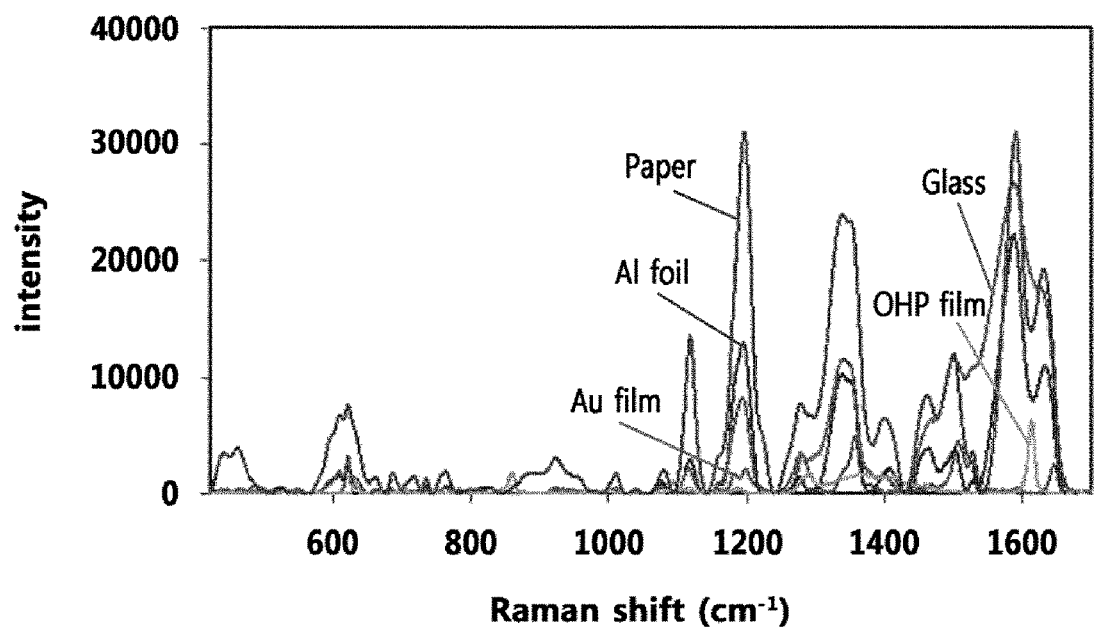
FIG. 14 shows the results of the Raman shift spectra of 1 mM RhB spread as a Raman-active material on a substrate comprising gold nanoparticles, which was prepared by the continuous chemical reaction method based on aluminum foil, glass, PET film (OHP film), and thin gold film as well as paper.

As shown in FIG. 14, the SERS substrate which was prepared by applying the continuous chemical reaction method on the paper showed significantly improved Raman signal measurement compared to those of other substrates.

Experimental Example 10: Reproducibility of Raman Signal Measurement According to Type of Substrates To confirm the reproducibility of the signal by repeated measurements, the substrates prepared according to Example 3 and Comparative Examples 1 and 2, were coated with RhB at a concentration of 1 mM, and the intensity with respect to Raman shift wavenumber was observed. Measurements were repeatedly performed 5 times under the same conditions as in Experimental Example 9, and the graphs obtained from each measurement were superimposed on each other and shown in FIG. 15.

As shown in FIG. 15, when the substrate according to Example 3 (indicated as "Paper" in FIG. 15) was used, a constant peak intensity was observed even after repeated measurements; however, when the substrates according to Comparative Examples 1 and 2 were used (indicated as "Al foil" and "Glass" in FIG. 15, respectively), there was a significant deviation with respect to the intensities measured in each measurement. This is consistent with the non-uniform distribution of gold nanoparticles on the aluminum foil substrate and the glass substrate confirmed in FIG. 12. That is, since gold nanoparticles that can exhibit the SERS effect are non-uniformly distributed on the substrate, even within the same substrate, the SERS effects are exhibited differently from the substrates prepared depending on the measurement position or, even when prepared under the same methods and conditions, the number of preparation, thus suggesting that the reproducible analysis is impossible.

Figure 16:
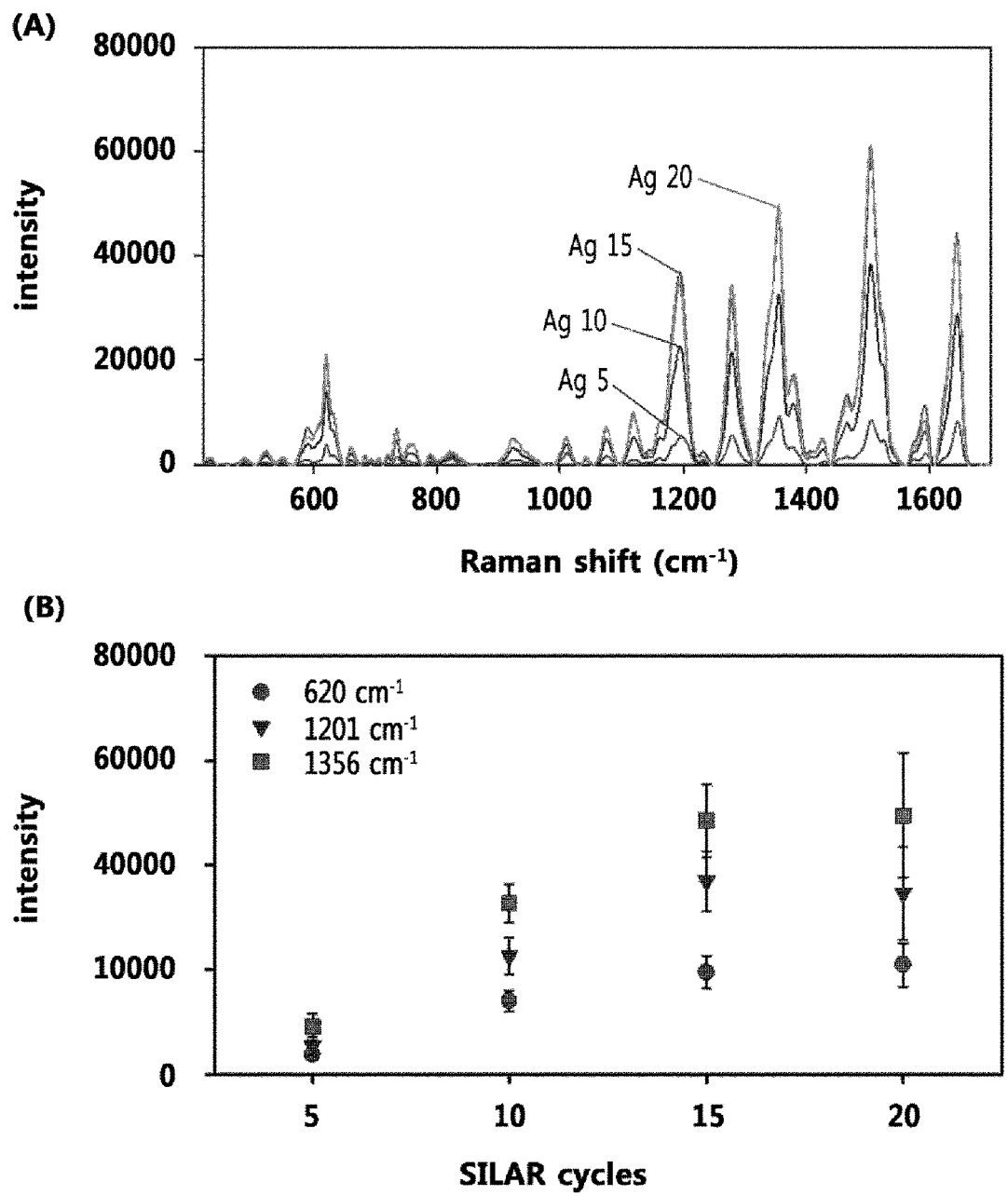
FIGS. 16A-B show the results with respect to the Raman signal enhancement effect on paper-based SERS substrates containing silver nanoparticles, which were prepared by performing the continuous chemical reaction method while increasing the number of repetitions of the method from 5 times to 20 times at intervals of 5 times.

Experimental Example 11: Effects of Raman Signal Enhancement According to Number of Repetitions of Continuous Chemical Reaction Method Raman signals were measured using the paper-based SERS substrates comprising silver nanoparticles prepared from Example 2 while increasing the number of repetitions of the continuous chemical reaction method from 5 times to 20 times by 5 times per increase, and the results are shown in FIGS. 16A-B. As shown in FIGS. 16A-B, it was confirmed that the measured Raman intensity increased as the repetition frequency increased. Additionally, it was confirmed that the increase pattern was different according to the wavenumber at which measurement was performed. This indicates that it is possible to explore conditions that can maximize the increase rate of signals by adjusting the number of repetitions according to the wavenumber to be measured. That is, these results suggest that it is possible to discover the optimal conditions that can maximize the Raman signal enhancement effect by appropriately combining the wavenumber for measurement, the number repetitions of the continuous chemical reaction method, etc.

Example 5: Preparation of Paper-Based SERS Substrate on which Bimetallic Nanoparticles (Au@AgNP) are Adsorbed Using Continuous Chemical Reaction Method Silver nanoparticles were formed on a paper substrate in the same manner as in Example 3 using an aqueous solution of 20 mM AgNO$_3$ as a silver precursor and a NaBH$_4$ solution as a reducing agent. Silver nanoparticles were allowed to grow to a predetermined size by repeating the entire process of immersing them in each of the solutions for 30 seconds followed by washing 6 times. Then, the silver nanoparticles formed on the paper substrate were allowed to form composite bimetallic nanoparticles using an aqueous solution of 1 mM HAuCl$_4$ as a gold precursor. As is the case with the silver nanoparticles, the substrate with silver nanoparticles was immersed in each of the solutions for 30 seconds to adsorb gold precursor ions and reduced to form gold nanoparticles, and the entire process was repeatedly performed 1 to 5 times for each solution to prepare 5 different kinds of samples. As a control, a substrate comprising only silver nanoparticles, which was not treated with a gold precursor ion and a reducing agent, was used.

Figure 17:
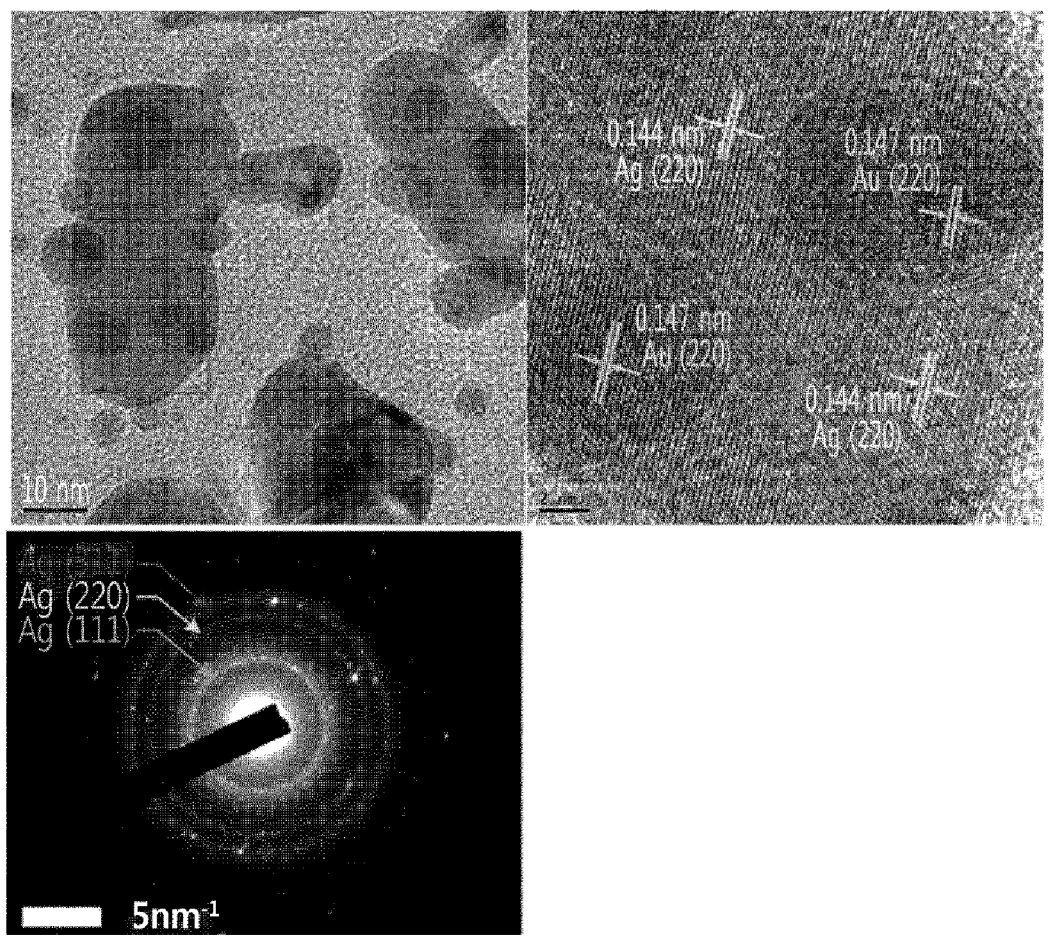
FIG. 17 shows the images with respect to the formation of gold-silver composite bimetallic nanoparticles (Au@AgNP), which were introduced on paper-based SERS substrates according to the continuous chemical reaction method, confirmed by TEM and selected area (electron diffraction; SAD or SAED).

The shape of the gold-silver composite bimetallic nanoparticles adsorbed to a paper substrate was observed by TEM and the crystallinity was analyzed by SAED. The results are shown in FIG. 17. As shown in FIG. 17, it was confirmed that the gold-silver composite bimetallic nanoparticles were shown to have relatively small-sized gold nanoparticles on the silver nanoparticles and thus have an overall raspberry-like shape. In particular, it was confirmed that the gold and silver particles have a lattice space of 0.147 nm (Au 220 grating) and 0.144 nm (Ag 220 grating), respectively. Furthermore, the results of the SAED analysis also showed that the silver nanoparticles formed by the continuous chemical reaction method according to the present invention have a proper crystalline structure.

Figure 18:
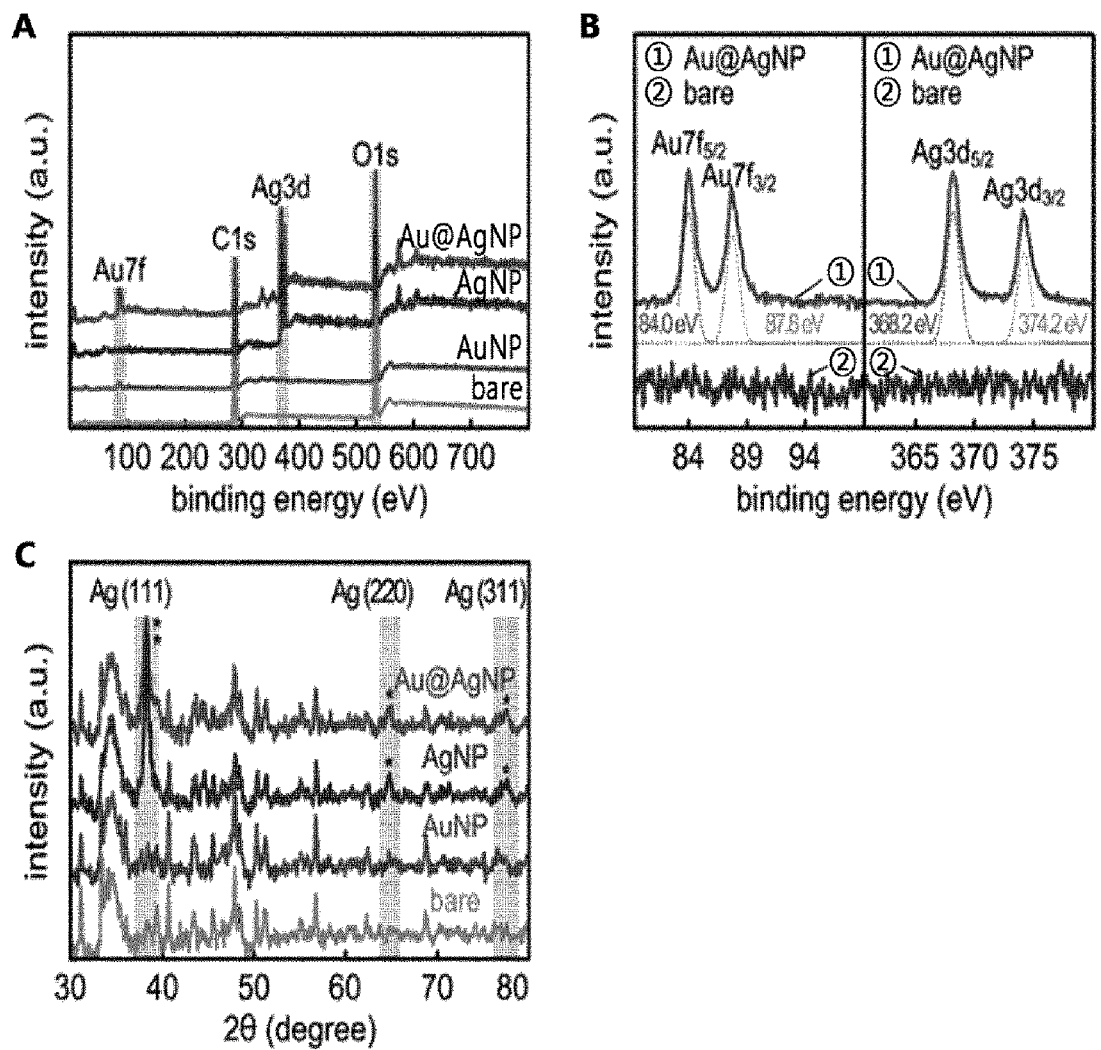
FIGS. 18A-C show the analysis results of paper-based SERS substrates on which gold-silver composite bimetallic nanoparticles were introduced according to the continuous chemical reaction method, with respect to the XPS analysis of the binding of the bimetallic nanoparticles to the paper substrates (A) and (B), and the XRD analysis of crystalline structures of each component (C).

Additionally, the binding of gold-silver composite bimetallic nanoparticles on a paper substrate was confirmed by XPS analysis and the results are shown in FIGS. 18A and 18B. The crystalline structure of each component of the gold-silver composite bimetallic nanoparticles was again confirmed by XRD analysis and the results are shown in FIG. 18C.

Experimental Example 12: Effects of Raman Signal Enhancement by Bimetallic Nanoparticles Rhodamine 6G (R6G) used as a SERS probe was prepared for each concentration from 1 fM ($1 \times 10^{-15}$ M) to 1 mM ($1 \times 10^{-3}$ M) and treated to a paper-based SERS substrate comprising gold-silver composite bimetallic nanoparticles prepared according to Example 5, and Raman signals were measured and the results are shown in FIGS. 19A to 19C, and an enhancement factor (EF), which is a criterion for the SERS effect, was derived therefrom. As shown in FIGS. 19B and 19C, when Raman signals were measured on the paper-based SERS substrate comprising gold-silver composite bimetallic nanoparticles according to the present invention, the Raman signals could be detected down to the level of 1 fM, and the calculated EF was about $10^{12}$, thus confirming that the SERS effect by the paper-based SERS substrate comprising gold-silver composite bimetallic nanoparticles according to the present invention is very excellent.

Additionally, to confirm the stability of the paper-based SERS substrate comprising gold-silver composite bimetallic nanoparticles according to the present invention, the change of intensity of the prepared substrates was confirmed by measuring the Raman signals on the day of preparation and on day 1, day 3, day 7, day 15, and day 30, respectively. As the control group, a substrate to which only silver nanoparticles were adsorbed was used. The Raman spectrum was measured at each of the above points and the results are shown in FIGS. 19D to 19F. As shown in FIGS. 19D to 19F, the paper-based SERS substrate comprising gold-silver composite bimetallic nanoparticles according to the present invention showed significantly higher Raman intensity at all measurement points compared to the substrate containing silver nanoparticles. In particular, in the case of a substrate comprising silver nanoparticles, the intensity of Raman signals decreased rapidly with time, for example, a decrease in the Raman signal measured at less than half of the 3 days after preparation. However, in the case of using the paper-based SERS substrate comprising gold-silver composite bimetallic nanoparticles according to the present invention, there was almost no decrease in the intensity of the measured Raman signal even until 30 days after the preparation. These results confirm that the use of the gold-silver composite bimetallic nanoparticles enables not only exhibiting a synergistic SERS effect but overcoming the drawbacks of silver, which is vulnerable to oxidation.

Figure 20:
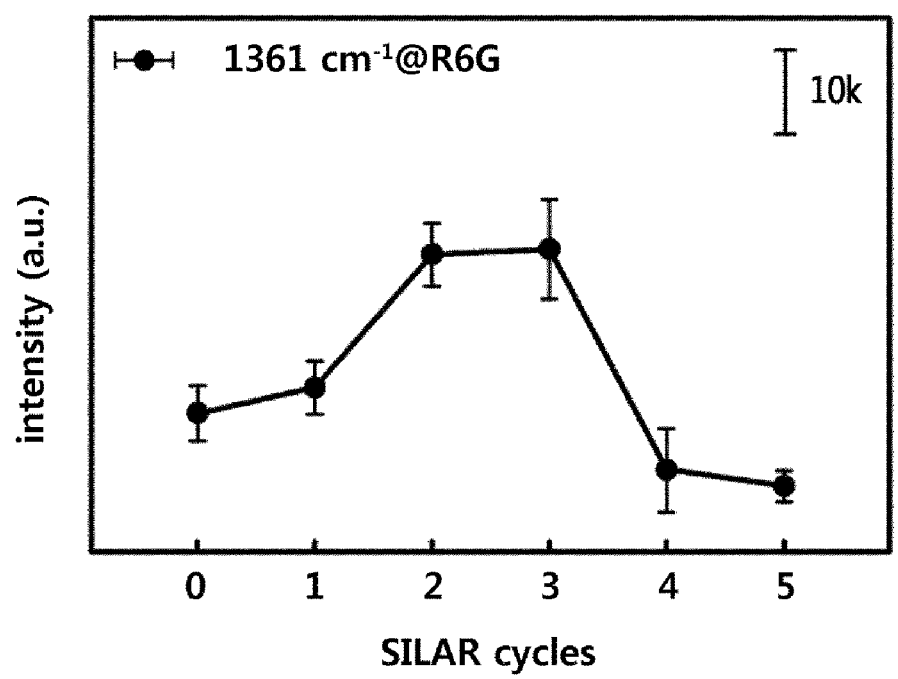
FIG. 20 shows the results with respect to the changes in Raman intensity according to the number of repetitions of the process of forming gold nanoparticles, when the paper-based SERS substrates, on which gold-silver composite bimetallic nanoparticles were introduced by the continuous chemical reaction method, are prepared.

In Example 5, R6G was treated to the control and the 5 different types of samples prepared by varying the number of repetitions of forming gold nanoparticles, and the intensity of Raman signals was measured at 1361 $cm^{-1}$. The results are shown in FIG. 20. As shown in FIG. 20, it was confirmed that when the process of forming gold nanoparticles was performed 2 to 3 three times, gold nanoparticles were formed at an appropriate density and size, thereby exhibiting the maximum SERS effect.

Conclusively, the paper-based SERS substrate prepared by the continuous chemical reaction method according to the present invention can not only exhibit a remarkable effect of Raman signal enhancement but also can provide a reproducible signal, and thus it can be effectively used as an analytical substrate using Raman spectroscopy.

The invention claimed is:

1. A method for preparing a paper-based surface-enhanced Raman Scattering (SERS) substrate which comprises metal nanoparticles having a diameter of 1 nm to 100 nm uniformly distributed and adsorbed in a designed pattern, the method comprising:
   step (1) of immersing a paper substrate in a precursor solution of a $1^{st}$ metal for the adsorption of precursors of the $1^{st}$ metal on the substrate;
   step (2) of immersing the paper substrate, on which the precursors of the $1^{st}$ metal are adsorbed, in a $1^{st}$ buffer for washing;
   step (3) of immersing the washed paper substrate in a solution of a Pt reducing agent to form nanoparticles of the Pt metal; and
   step (4) of immersing the nanoparticles of the $1^{st}$ metal grown on the paper substrate in a $1^{'th}$ buffer for washing.

2. The method of claim 1, wherein steps (1) to (4) are repeatedly performed 2 to 10 times.

3. The method of claim 1, further comprising:
   step (1)' of immersing the paper substrate obtained from step (4) in a precursor solution of a $2^{nd}$ metal for the adsorption of $2^{nd}$ metal precursors on the substrate;
   step (2)' of immersing the paper substrate, on which the $2^{nd}$ metal precursors are adsorbed, in a $2^{nd}$ buffer for washing;
   step (3)' of immersing the washed paper substrate in a solution of a $2^{nd}$ reducing agent to form nanoparticles of the $2^{nd}$ metal; and
   step (4)' of immersing the nanoparticles of the $2^{nd}$ metal grown on the paper substrate in a $2^{'th}$ buffer for washing.

4. The method of claim 3, wherein steps (1)' to (4)' are repeatedly performed 2 to 5 times.

5. The method of claim 3, wherein steps (1)' and (3)' are each independently performed for 10 to 120 seconds.

6. The method of claim 1, wherein steps (1) and (3) are each independently performed for 10 to 120 seconds.

7. The method of claim 1, wherein a pattern is formed on the paper substrate by treating an area other than the SERS-active area with a hydrophobic material.

8. The method of claim 1, wherein the precursor solutions of the $1^{st}$ metal and $2^{nd}$ metal are different from each other, and the $1^{st}$ and $2^{nd}$ metal precursor solutions are aqueous solutions comprising the $1^{st}$ and $2^{nd}$ metals in an ionic state, respectively.

9. A method for preparing a paper-based surface-enhanced Raman Scattering (SERS) substrate which comprises metal nanoparticles having a diameter of 1 nm to 100 nm uniformly distributed in a designed pattern and further comprises carboxymethylcellulose, the method comprising:
   step (1) of preparing a solution of metal nanoparticles by mixing metal nanoparticles and an aqueous solution of carboxymethylcellulose, wherein the solution of metal nanoparticles has a viscosity of 500 cP to 10,000 cP;
   step (2) of preparing a paper substrate on which a desired pattern is formed; and
   step (3) of coating the solution of metal nanoparticles of step (1), on the paper substrate, wherein an outwardly-directed surface tension at an interface of the pattern is inhibited.

10. The method of claim 9, wherein the metal nanoparticles have a uniform size with an average diameter of 10 nm to 100 nm.

11. The method of claim 9, wherein the aqueous solution of carboxymethylcellulose has a concentration of 0.7 wt % to 2.5 wt %.

12. The method of claim 9, wherein the solution of metal nanoparticles is prepared by mixing metal nanoparticles and an aqueous solution of carboxymethylcellulose in a volume ratio of 1:5 to 1:10.

13. The method of claim 9, wherein step (2) is performed by coating with wax an area of paper, on which a desired pattern is designed, excluding the area with the desired pattern.

14. The method of claim 9, further comprising step (4) of drying by heating after step (3).

15. The method of claim 14, wherein steps (3) and (4) are repeatedly performed for a total of 1 to 5 times.

\* \* \* \* \*

UNITED STATES PATENT AND TRADEMARK OFFICE
CERTIFICATE OF CORRECTION

PATENT NO. : 10,379,053 B2
APPLICATION NO. : 15/578795
DATED : August 13, 2019
INVENTOR(S) : Sam Jin Choi et al.

Page 1 of 1

It is certified that error appears in the above-identified patent and that said Letters Patent is hereby corrected as shown below:

In the Claims

In Claim 1, Column 24, Line 19, delete "Pt" and insert --1$^{st}$-- therefor.

In Claim 1, Column 24, Line 20, delete "Pt" and insert --1$^{st}$-- therefor.

In Claim 1, Column 24, Line 22, delete "1′th" and insert --1$^{st}$-- therefor.

Signed and Sealed this
Eighth Day of October, 2019

Andrei Iancu
*Director of the United States Patent and Trademark Office*